US009814771B2

(12) United States Patent
Borca et al.

(10) Patent No.: US 9,814,771 B2
(45) Date of Patent: Nov. 14, 2017

(54) LIVE ATTENUATED CLASSICAL SWINE FEVER VACCINE BASED IN GENETIC MANIPULATION OF A PUTATIVE FUSION PEPTIDE AREA IN THE VIRUS STRUCTURAL GLYCOPROTEIN E2

(71) Applicant: The United States of America, as Represented by the Secretary of Agriculture, Washington, DC (US)

(72) Inventors: Manuel V. Borca, Westbrook, CT (US); Douglas P. Gladue, Guilford, CT (US); Lauren G. Holinka-Patterson, Deep River, CT (US); Vivian O'Donnell, Old Saybrook, CT (US); Jose Nieva, Bilboa (ES)

(73) Assignees: The United States of America, as represented by The Secretary of Agriculture, Washington, DC (US); The University of Connecticut, Farmington, CT (US); Universidad del Pais Vasco/Euskal Herriko Univertsitatea (UPV-EHU) (ES)

( * ) Notice: Subject to any disclaimer, the term of this patent is extended or adjusted under 35 U.S.C. 154(b) by 0 days.

(21) Appl. No.: 15/259,725

(22) Filed: Sep. 8, 2016

(65) Prior Publication Data

US 2017/0128563 A1 May 11, 2017

Related U.S. Application Data

(60) Provisional application No. 62/217,207, filed on Sep. 11, 2015.

(51) Int. Cl.

*A61K 39/187* (2006.01)
*C12N 7/00* (2006.01)
*A61K 39/00* (2006.01)

(52) U.S. Cl.

CPC .............. *A61K 39/187* (2013.01); *C12N 7/00* (2013.01); *A61K 2039/5256* (2013.01); *A61K 2039/552* (2013.01); *C12N 2770/24321* (2013.01); *C12N 2770/24334* (2013.01)

(58) Field of Classification Search

None

See application file for complete search history.

(56) References Cited

U.S. PATENT DOCUMENTS 8,846,055 B2 * 9/2014 Borca .................... A61K 39/12 424/204.1
2017/0128563 A1 * 5/2017 Borca .................. A61K 39/187

OTHER PUBLICATIONS

Fernandez-Sainz et al. (Virology. 2014; 456-157: 121-130).*
Garry and Dash (Virology. 2003; 307: 255-265).*
Sequence alignment of instant SEQ ID No. 1 with geneseq database access No. AXF15010 by Borca et al in USPgPub 2009181051 on Aug. 2009.*
Sequence alignment of instant SEQ ID No. 2 with geneseq database access No. AXF15012 by Borca et al in USPgPub 2009181051 on Aug. 2009.*

* cited by examiner

*Primary Examiner* — Shanon A Foley

(74) *Attorney, Agent, or Firm* — John D. Fado; Mark D. McNemar

(57) ABSTRACT

The role of a specific E2 region containing a putative fusion peptide (FP) sequence was evaluated. FPs critically contribute to the interaction between proteins and the membrane system of the host cell. Reverse genetics utilizing a full-length infectious clone of the highly virulent CSFV strain Brescia (BICv) was used to evaluate how amino acid substitutions within this region of E2 may affect replication of BICv in cell cultures and affect virus virulence in swine. Interestingly, mutated virus FPi.c was completely attenuated when inoculated intranasally at a dose of $10^5$ TCID50 in swine. Importantly, animals infected with FPi.c virus were protected against the virulent challenge with Brescia virus at 3 and 28 days after vaccination. Protection was evidenced by absence of clinical signs related with CSF as well as the absence of viremia produced by the challenge virulent virus.

6 Claims, 3 Drawing Sheets

| E2 FPi.c Mutant virus (amino acid position in Brescia polypeptide) | | | | | | | | | | |
|---|---|---|---|---|---|---|---|---|---|---|
| | 869 | 870 | 871 | 872 | 873 | 874 | 875 | 876 | 877 | 878 |
| **BICv** | C | K | W | G | G | N | W | T | C | V |
| **FPi.c** | C | K | T | G | G | N | D | T | C | T |

Fig. 1

LIVE ATTENUATED CLASSICAL SWINE FEVER VACCINE BASED IN GENETIC MANIPULATION OF A PUTATIVE FUSION PEPTIDE AREA IN THE VIRUS STRUCTURAL GLYCOPROTEIN E2

This application claims the benefit of U.S. Provisional Application No. 62/217,207 filed Sep. 11, 2015, which is incorporated herein by reference in its entirety.

BACKGROUND OF THE INVENTION

Field of the Invention

This invention relates to the construction of a recombinant Classical Swine Fever Virus (CSFV) live attenuated candidate strain vaccine, FPi.c. The FPi.c virus contains mutations in three amino acid residues within the fusion peptide (FP) region of CSFV E2 comprising amino acid residues 869-878 resulting in the mutations: W871T, W875D, and V878T.

Description of the Relevant Art

Classical swine fever (CSF) is a highly contagious disease of swine caused by CSF virus (CSFV), a small enveloped virus with a positive-sense, single-strand RNA genome. CSFV is classified as a member of the pestivirus genus within the Flaviviridae family along with other viruses of economic importance, bovine viral diarrhea virus (BVDV) and border disease virus (BDV) (Becher et al. 2003. *Virology* 311: 96-104). The approximately 12.5-kb CSFV genome contains a single open reading frame that encodes a polyprotein composed of 3,898 amino acids that ultimately yields up to 12 final cleavage products (NH2-Npro-C-Erns-E1-E2-p7-NS2-NS3-NS4A-NS4B-NS5A-NS5B-COOH) through co- and post-translational processing of the polyprotein by cellular and viral proteases (Rice, C. M. 1996. In: *Fundamental Virology,* 3rd edition, Fields and Howley, eds., Lippincott Raven, Philadelphia, pp. 931-959).

Structural components of the virion include the capsid (C) protein and glycoproteins: $E^{rns}$, E1 and E2. $E^{rns}$, a secreted protein that demonstrates RNAse activity and is loosely associated with the viral envelope (Thiel et al. 1991. *J. Virol.* 65: 4705-4712; Weiland et al. 1990. *J. Virol.* 64: 3563-3569; Weiland et al. 1999. *J. Gen. Virol.* 80: 1157-1165) does not have a hydrophobic transmembrane anchor domain. $E^{rns}$ does, however, possess a C-terminal charged amphipathic segment that can mediate translocation of $E^{rns}$ across bilayer membranes (Langedijk, J. P. 2002. *J. Biol. Chem.* 277:5308-5314). E1 and E2 are transmembrane proteins with an N-terminal ectodomain and a C-terminal hydrophobic anchor (Thiel et al. 1991, supra). E2 is considered essential for CSFV replication, as virus mutants containing partial or complete deletions of the E2 gene are nonviable (van Gennip et al. 2002. Vaccine 20:1544-1556). E2 has been implicated, along with $E^{rns}$ (Hulst and Moorman. 1997. *J. Gen. Virol.* 78 (Pt 11): 2779-2787) and E1 (Wang et al. 2004. *Virol.* 330:332-341), in viral adsorption to host cells (Liang et al. 2003. *J. Gen. Virol.* 84:1269-1274; Van Gennip et al. 2000. *Vaccine* 19:447-459). Modifications introduced into this glycoprotein appear to have an important effect on CSFV virulence (Risatti et al. 2005. *J. Virol.* 79: 3787-3796; Risatti et al, 2006. *Virology* 355: 94-101; Risatti et al. 2007. *J. Virol.* 81: 924-933.; Van Gennip et al. 2004. *J. Virol.* 78: 8812-8823).

Using proteomic computational analysis, E2 has been characterized as a truncated class II fusion protein (Garry and Dash. 2003. *Virol.* 307:255-265). Although the overall structures of class I and II fusion proteins are distinct, they may share structural/functional characteristics in the parts of the molecules that interact with and disrupt bilayer membranes. It is well established that class I fusion proteins have a fusion peptide at the amino terminus of the molecule, or close to it, that is critical for fusion (Gallaher, W. R. 1987. *Cell* 50:327-328; Gallaher, W. R. 1996. *Cell* 85:477-478; Gallaher et al. 1989. *AIDS Res. Human Retroviruses* 5:431-440; Gallaher et al. 2001. *BMC Microbiol.* 1:1). Class II fusion proteins have an internal FP that is located after secondary structural folding at distal locations from the transmembrane anchor (Kuhn et al. 2002. *Cell* 108:717-725; Lescar et al. 2001. *Cell* 105:137-148; Rey et al. 1995. *Nature* 375:291-298)

Strategies for controlling disease in the event of a CSFV outbreak include the production of rationally designed live attenuated vaccine CSFV strains. Here, we report the effects of modifying a region within the CSFV structural glycoprotein E2, a region which contributes to the interaction between E2 and the host cell membrane.

SUMMARY OF THE INVENTION

We have developed a novel classical swine fever mutant virus, the FPi.c virus, by modifying the fusion peptide region of the CSFV structural protein E2.

In accordance with this discovery, it is an object of the invention to provide a recombinant CSFV mutant virus, the FPi.c virus, containing mutations in three amino acids within the fusion peptide region of CSFV E2 (amino acids 869-878) resulting in the mutations W871T, W875D and V878T. The nucleotide sequence of FP2i.c (SEQ ID NO:1) differs from the nucleotide sequence encoding the BICv (SEQ ID NO:3). SEQ ID NO:1 encodes the protein sequence of SEQ ID NO:2 comprising the mutated amino acids at positions 871, 875 and 878. SEQ ID NO:3 encodes the non-mutated, wild-type amino acids of a protein having SEQ ID NO:4.

An added object of the invention is to provide immunogenic compositions comprising a viable recombinant classical swine fever virus mutant, FPi.c.

An additional object of the invention is to provide a rationally designed live attenuated mutant CSFV, the FPi.c, effective to protect an animal from clinical CSF disease when challenged with virulent Brescia CSFV.

A still further object of the invention is to provide a rationally designed live attenuated mutant CSFV, the FPi.c, effective to inhibit the interaction between the fusion protein region of CSFV E2 and the host cell membrane.

Another object of the invention is to provide a method for protecting an animal against CSF by administering an effective amount of rationally designed live attenuated mutant CSFV, the FPi.c, vaccine.

Other objects and advantages of this invention will become readily apparent from the ensuing description.

BRIEF DESCRIPTION OF THE DRAWINGS

FIG. 1 depicts the sequence alignment to show changes in the amino acid residues in that area of E2 containing the predicted fusion peptide in the FPi.c (Fusion Peptide infectious clone (amino acid residues 869-878 of SEQ ID NO:2)) as related to the E2region of the highly virulent CSFV strain Brescia (BICv (SEQ ID NO:5)).

DETAILED DESCRIPTION OF THE INVENTION

Figure 2:
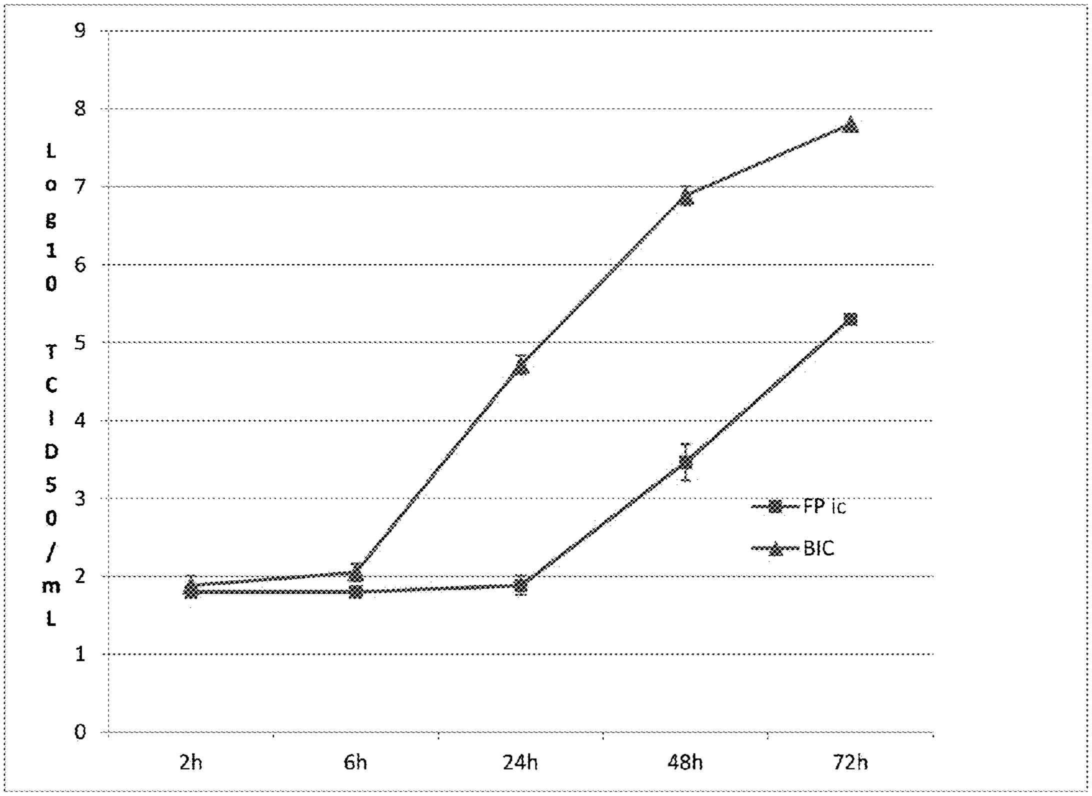
FIG. 2 shows in vitro growth characteristics of FPi.c mutant virus and parental BICv. SK6 cell cultures were infected (MOI=0.01) with either FPi.c virus mutants or BICv and virus yield was titrated at times post infection in SK6 cells. Data represent means and standard deviations from two independent experiments. Sensitivity of virus detection: ≥1.8 $TCID_{50}$/ml.

Here we evaluate the role of a specific E2 region, $^{869}$CKWGGNWTCV$^{878}$ (SEQ ID NO:5), containing a putative fusion peptide (FP) sequence. Fusion peptides critically contribute to the interaction between proteins and the membrane system of the host cell. Viral internal fusion peptides (IFPs) usually form connecting loops in β-domains. They are therefore enriched in glycine residues, and often stabilized through disulfide bridges. More importantly, at the apex, they are exposed to solvent hydrophobic-at-interface aromatic residues (prominently tryptophan) that enable glycoprotein insertion into the target cell membrane.

The mean interfacial hydrophobicity (sliding window of 5 aa) was calculated for the CSFV E2 sequence using Wimley-White algorithms. E2 crystal structures of closely related Bovine Viral Diarrhea Virus Genotype 1 (BVDV1) obtained at pH 8.0 and 5.0(PDB IDs 2YQ2 and 2YQ3) were subsequently used to localize solvent-exposed connecting turns displaying high interfacial hydrophobicity, and possibly being stabilized through disulfide bridge formation. Given these particular considerations, the CSFV E2FPII region was defined to comprise E2 residues $^{869}$ CKWGGNWTCV$^{878}$ (SEQ ID NO:5).

Mutations to render an infectious clone (i.c) variant were selected on the following grounds: abating hydrophobicity on solvent-exposed E2FPII positions (i.e., reducing the interfacial hydropathy index), while minimizing the impact on global stability of the protein (as inferred from the 2YQ2 crystal structure, and using the "Prediction of Protein Mutant Stability Changes" server). Thus, three non-conservative changes were made as follows: W871 T, W875D and V879T. The resulting mutation is predicted to fold properly upon translation, but to be incapable to insert into the target cell membrane and promote fusion.

Reverse genetics utilizing a full-length infectious clone of the highly virulent CSFV strain Brescia (BICv) was used to evaluate how amino acid substitutions within this region of E2 may affect replication of BICv in cell cultures and virus virulence in swine. A recombinant CSFV, FPi.c, containing mutations in three amino acid residues within the E2 protein area comprising CSFV amino acid residues 869-878 was constructed resulting in the following changes: W871T, W875D, and V878T.

The nucleotide sequence of FPi.c (SEQ ID NO:1) differs from the nucleotide sequence encoding the highly virulent CSFV strain BICv (SEQ ID NO:3). The new virus, FPi.c, possesses the same amino acid sequence as BICv except for three substitutions in the FP region comprising amino acids 869-878; namely, the substitution of tryptophan by threonine at position 871, the substitution of tryptophan by aspartic acid at position 875, and the substitution of valine by threonine at position 878. The nucleotide sequence of FPi.c (SEQ ID NO:1) encodes the polypeptide sequence (SEQ ID NO:2).

Interestingly, mutated virus FPi.c was completely attenuated when inoculated intranasally at a dose of $10^5$ $TCID_{50}$ in swine. Importantly, animals infected with FPi.c virus were protected against the virulent challenge with Brescia virus at either 3 or 28 days after vaccination. Protection was evidenced by absence of clinical signs related with CSF as well as the absence of viremia produced by the challenge virulent virus.

A vaccine is defined herein as a biological agent which is capable of providing a protective response in an animal to which the vaccine has been delivered and is incapable of causing severe disease. Administration of the vaccine results in immunity from a disease; the vaccine stimulates antibody production or cellular immunity against the pathogen causing the disease. Immunity is defined herein as the induction of a significant higher level of protection in a population of swine against mortality and clinical symptoms after vaccination compared to an unvaccinated group. In particular, the vaccine according to the invention protects a large proportion of vaccinated animals against the occurrence of clinical symptoms of the disease and mortality. The vaccine of the invention herein is a genetically engineered mutant virus vaccine. A mutation is understood to be a change in the genetic information of a "wild-type" or unmodified E2 gene of a parent CSFV strain which is able to express native E2 proteins. Thus, the E2 polypeptide expressed by the FPi.c mutant virus is changed. The FPi.c recombinant classical swine fever virus (CSFV) mutant comprising DNA encoding a mutation in CSFV E2 glycoprotein, wherein the mutation comprises three substitutions in the FP region: the substitution of tryptophan by threonine at position 871, the substitution of tryptophan by aspartic acid at position 875, and the substitution of valine by threonine at position 878.

A vaccine against CSFV is provided that comprises a FPi.c virus mutant as defined above in a live form, and a pharmaceutically acceptable carrier or diluent. The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA (sucrose, phosphate, glutamate, and human. albumin), carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated CSFV vaccines. Briefly, a susceptible substrate is inoculated with the FPi.c mutant and propagated until the virus has replicated to a desired titer after which FPi.c-containing material is harvested. Subsequently, the harvested material is formulated into a pharmaceutical preparation with immunizing properties.

Every substrate which is able to support the replication of FPi.c viruses can be used in the present invention, including Swine kidney cells (SK6) and primary cultures of swine peripheral blood macrophages.

The vaccine may be administered by intramuscular, intradermal, subcutaneous or intranasal inoculation or injection in an amount which is effective to protect the animal against challenge by a virulent strain of CSFV. This amount may vary according to the animal being inoculated, taking into consideration the size and weight of the animal. The vaccine according to the invention comprises an effective dosage of the FPi.c mutant as the active component, i.e. an amount of immunizing FPi.c material that will induce immunity in the vaccinated animals, swine, against challenge by a virulent CSFV. Immunity is defined herein as the induction of a significant higher level of protection in a population of swine against mortality and clinical symptoms after vaccination compared to an unvaccinated group. In particular, the vaccine according to the invention prevents a large proportion of vaccinated animals against the occurrence of clinical symptoms of the disease and mortality. Typically, the live vaccine can be administered in a dose of $10^4$-$10^5$ $TCID_{50}$. Effective amounts may be experimentally determined as necessary by those of skill in the art by following the guidance provided, for example, by Examples 6 and 7.

In addition to the FPi.c mutant, the invention can also include combination vaccines comprising a vaccine strain capable of inducing protection against another porcine pathogen.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al. 1990. *Dtsch. Tierarztl. Wochenschr.* 97: 77-79), free of BVDV, were cultured in Dulbecco's minimal essential media (DMEM) (Gibco, Grand Island, N.Y.) with 10% fetal calf serum (FCS) (Atlas Biologicals, Fort Collins, Colo.). CSFV Brescia strain was propagated in SK6 cells and was used for the construction of an infectious cDNA clone (Risatti et al. 2005, supra). Growth kinetics was assessed using primary swine macrophage cell cultures prepared as described by Zsak et al. (*J. Virol.* 70:8865-8871). Titration of CSFV from clinical samples was performed using SK6 cells in 96-well plates (Costar, Cambridge, Mass.). After 4 days in culture, viral infectivity was assessed using an immunoperoxidase assay utilizing the CSFV monoclonal antibody WH303 (mAb WH303) (Edwards et al. 1991. *Vet. Microbiol.* 29:101-109) and the Vectastain ABC kit (Vector Laboratories, Burlingame, Calif.). Titers were calculated according to the method of Reed and Muench (1938. *Amer. J. Trop. Med. Hygiene* 27:493-497) and expressed as $TCID_{50}$/ml. As performed, test sensitivity was $\geq \log_{10}$ 1.8 $TCID_{50}$/ml.

Example 2

CSFV Infectious Clones Harboring Amino Acid Substitutions in Fusion Peptide Sequence To evaluate the role of the putative Fusion Peptide (FP) in the in vitro and in vivo replication of CSFV as well as in the production of disease in swine, a recombinant CSFV containing three amino acid substitutions in the FP area was designed using a full-length cDNA infectious clone (IC) of the virulent Brescia strain (BICv) as a template (FIG. 1 and Table 1). The recombinant CSFV, named FPi.c, was constructed and harbors substitutions in three amino acid residues, W871T, W875D, and V878T, within the E2 protein area comprising CSFV amino acid residues 869-878. Constructs containing mutations in the FP area were obtained using the QuickChange XL Site-Directed Mutagenesis kit (Stratagene) performed per manufacturer's instructions using full-length pBIC as template and the primers described in Table 1. The product was then digested with Dpn1, leaving only the newly amplified plasmid, transformed into XL10-Gold ultracompetent cells, and grown on Terrific Broth Agar Plates with ampicillin (Teknova). Positive colonies were selected for by sequence analysis of the E2 gene and grown for plasmid purification using a Maxiprep kit (Qiagen Sciences, MD). Each of the IC constructs was completely sequenced to verify that only site-directed mutagenesis-induced changes were present.

TABLE 1

Nucleotide sequence of primers used for the production of FPi.c recombinant viruses.

| Mutant Name | Primer Sequence | SEQ ID NO: |
|---|---|---|
| Fi.b | 5'-attctactgtaaatggggggggcaatgatacat gtacgaaaggtgaaccagtgacctacacg-3' | 6 |
| Ri.b | 5'-cgtgtaggtcactggttcacctttcgtacatg tatcattgccccccccatttacagtagaat-3' | 7 |
| Fi.c | 5'-tggaaaatgaagatctattctactgtaaaacg gggggcaatgatac-3' | 8 |
| Ri.c | 5'-gtatcattgccccccgttttacagtagaatag atcttcattttcca-3' | 9 |

Example 3

In Vitro Rescue of CSFV Brescia and FP Mutants

Full-length genomic clones were linearized with SrfI and in vitro transcribed using the T7 Megascript system (Ambion, Austin, Tex.) (Risatti et al. 2005, supra). RNA was precipitated with LiCl and transfected into SK6 cells by electroporation at 500 volts, 720 ohms, 100 watts with a BTX 630 electroporator (BTX, San Diego, Calif.). Cells were seeded in 12-well plates and incubated for 4 days at 37° C. and 5% $CO_2$. Virus was detected by immunoperoxidase staining as described above, and stocks of rescued viruses were stored at −70° C. Full length nucleotide sequence of FPi.c rescued mutant viruses was performed to ensure the presence of the predicted mutations (data not shown).

Example 4

DNA Sequencing and Analysis

Full-length infectious clones and in vitro rescued viruses were completely sequenced with CSFV-specific primers by the dideoxynucleotide chain-termination method (Sanger et al. 1977. *Proc. Natl. Acad. Sci. USA* 74: 5463-5467). Viruses recovered from infected animals were sequenced in the region of the genome that contained the desired mutations. Sequencing reactions were prepared with the Dye Terminator Cycle Sequencing Kit (Applied Biosystems, Foster City, Calif.). Reaction products were sequenced on a PRISM 3730xl automated DNA Sequencer (Applied Biosystems). Sequence data were assembled using Sequencher 4.7™ software (Genes Codes Corporation, Ann Arbor, Mich.). The final DNA consensus sequence represented, on average, a three- or four-fold redundancy at each base position.

Example 5

Replication of the CSFV FP2i.c Mutants In Vitro

In vitro replication characteristics of the FPi.c mutant viruses relative to parental BICv was evaluated in a multiple-step growth curve. SK6 cell cultures were infected at a MOI of 0.01 $TCID_{50}$ per cell. Viruses were adsorbed for 1 hour (time zero), and samples were collected at 72 hours post-infection and titrated in SK6 cell cultures. FPi.c mutant virus exhibited significant decreased growth kinetics when compared with the parental BICv (FIG. 2). Depending of the time point considered, FPi.c produced virus yields approximately 100 times lower than BICv. Therefore, residues W871, W875, and V878 of the CSFV polypeptide do significantly affect the ability of the virus to replicate in cell cultures.

Example 6

Animal Studies: Virulence of CSFV FPi.c Mutants In Vivo

Virulence of FPi.c mutant viruses relative to BICv was assessed in 10 to 12 weeks old, forty-pound commercial-breed pigs inoculated intranasally (IN) with $10^5$ $TCID_{50}$ of either FPi.c or BICv virus. Clinical signs (anorexia, depression, purple skin discoloration, staggering gait, diarrhea and cough) and changes in body temperature were recorded daily throughout the experiment and scored as previously described (Mittelholzer et al. 2000. *Vet. Microbiol.* 74:293-308). Blood was collected at times post-infection from the anterior vena cava into EDTA-containing tubes (Vacutainer).

To examine whether alterations of the residues residing in the putative FP of glycoprotein E2 affect virulence, a group of pigs was intranasally inoculated with approximately $10^5$ $TCID_{50}$ of CSFV FPi.c virus mutant and monitored for clinical disease, evaluated relative to parental BICv. All animals infected with BICv presented clinical signs of CSF starting 3 to 4 days post-infection (DPI), developing classic symptoms of the disease and dying around 7-8 DPI (Table 2). Conversely, FPi.c mutant virus presented a completely attenuated phenotype (Table 2). All FPi.c infected animals remained clinical normal until the end of the observational period (21 days post infection).

TABLE 2

Swine survival and fever response following infection with FPi.c mutant virus and parental BICv.

| Virus | No. of Survivors/ Total No. | Mean time to Death (days ± SD) | Fever: No. of days to onset (days ± SD) | Fever: Duration (days ± $SD^b$) |
|---|---|---|---|---|
| BIC | 0/5 | 7.12 (2) | 3.70 (1.2) | 4.9 (1.8) |
| FPi.c | 10/10 | — | — | — |

Figure 3:
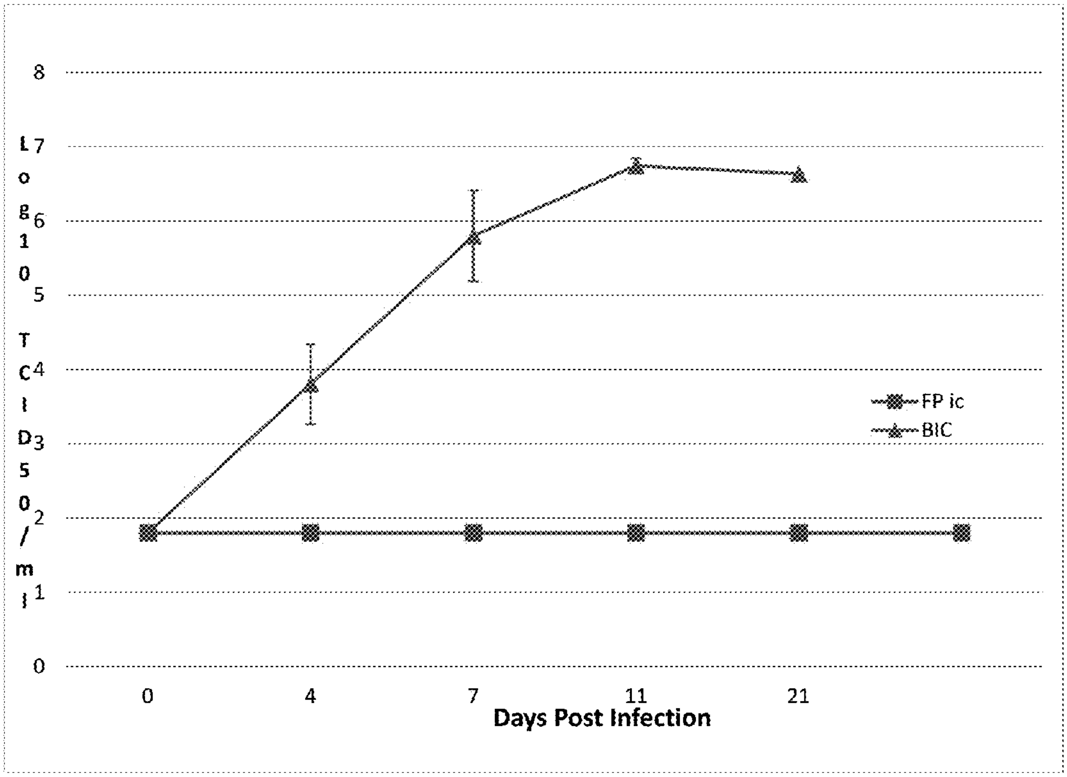
FIG. 3 depicts viremia in animals infected with either FPi.c mutant virus or parental BICv. Data represent means and standard deviations from 5 animals. Sensitivity of virus detection: ≥1.8 $TCID_{50}$/ml.

Viremia in animals inoculated with either FPi.c mutant or parenteral BICv viruses in general accompanied the evolution of the clinical disease. BICv infected animals presented high viremia titers that remained until death of the animal. Conversely, animals infected with the FPi.c mutant virus presented undetectable viremia titers as evaluated until the end of the observational period (FIG. 3). Therefore, substitutions of residues W871, W875, and V878 of the CSFV polypeptide do significantly affect the ability of the virus to produce replicate and produce disease in in swine.

Example 7

FPi.c Virus Mutant Induces Protection Against Lethal CSFV Challenge

The limited in vivo replication kinetics shown by FPi.c virus mutant is similar to that observed with the vaccine virus that induces protection against BICv. In order to assess the ability of FPi.c to induce protection against CSFV, pigs (n=10) were inoculated with FPi.c virus and five of them challenged at 3 DPI and the other five at 28 DPI with virulent BICv. Mock-vaccinated control pigs receiving BICv only (n=5) developed anorexia, depression, and fever by 4 days post-challenge (DPC). Animals died or were euthanized in extremis by 9 DPC (Table 3). Conversely, animals inoculated with FPi.c virus remained clinically normal during the observational period. Only two animals challenged at 3 DPI showed a very transient and mild rise in body temperature. Pigs were protected against the challenge with BICv (Table 3). Challenge virus was undetectable in clinical samples obtained from any FPi.c virus-infected pigs that were challenged at 28 DPI (data not shown).

TABLE 3

Swine survival and fever response of animals infected with FPi.c mutant virus and challenged with parental BICv at either 3 or 28 dpi.

| Virus | No. of Survivors/ Total No. | Mean time to Death (days ± SD) | Fever: No. of days to onset (days ± SD) | Fever: Duration (days ± $SD^b$) |
|---|---|---|---|---|
| BIC | 0/5 | 8.85 (1.5) | 4.8 (1.2) | 5.2 (1.5) |
| FPi.c 3 DPI | 5/5 | — | — | — |
| FPi.c 28 DPI | 5/5 | — | — | — |

As a summary, we present here an approach for rationally developing an experimental live attenuated marker CSFV vaccine strain, FPi.c, demonstrate that genetic changes introduced in FPi.c produce a stabilization of its attenuated phenotype, and that FPi.c elicits solid protection against the challenge in animals vaccinated 3 or 28 days earlier.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant classical swine fever virus (CSFV) mutant, FPi.c, comprising cDNA encoding a mutated CSFV E2 glycoprotein of SEQ ID NO:2, wherein the mutated CSFV E2 glycoprotein comprises three substitutions in the FP region: the substitution of tryptophan by threonine at position 871, the substitution of tryptophan by aspartic acid at position 875, and the substitution of valine by threonine at position 878.

2. The recombinant CSFV mutant of claim 1 comprising cDNA having the sequence identified by SEQ ID NO: 1.

3. A vaccine composition comprising the recombinant CSFV mutant according to any one of claims 1 and 2.

4. An isolated cell infected with the CSFV mutant of any one of claims 1 and 2.

5. A method for the protection of swine against CSF, comprising administering to swine a live attenuated CSF vaccine comprising the recombinant CSFV mutant FPi.c according to claim 1 in an amount effective to protect said swine from clinical CSF.

6. A method for the protection of swine against CSF, comprising administering to swine a live attenuated CSF vaccine comprising the recombinant CSFV mutant FPi.c according to claim 2 in an amount effective to protect said swine from clinical CSF.

* * * * *

SEQUENCE LISTING

<160> NUMBER OF SEQ ID NOS: 9

<210> SEQ ID NO 1
<211> LENGTH: 12285
<212> TYPE: DNA
<213> ORGANISM: Classical Swine Fever Virus

<400> SEQUENCE: 1
agttcattct cgtgtacatg attggacaaa tcaaaatctc aatttggttc agggcctccc 60
tccagcgacg gccgagctgg gctagccatg cccacagtag gactagcaaa cggagggact 120
agccgtagtg gcgagctccc tgggtggtct aagtcctgag tacaggacag tcgtcagtag 180
ttcgacgtga gcagaagccc acctcgagat gctatgtgga cgagggcatg cccaagacac 240
accttaaccc tagcgggggt cgttagggtg aaatcacacc atgtgatggg agtacgacct 300
gatagggtgc tgcagaggcc cactattagg ctagtataaa aatctctgct gtacatggca 360
catggagttg aatcattttg aacttttata caaaacaaac aaacaaaaac caatgggagt 420
ggaggaaccg gtatacgatg taacggggag accattgttt ggagacccaa gtgaggtaca 480
cccacaatca acattgaagc taccacatga taggggggaga ggcaacatca aaacaacact 540
gaagaaccta cctaggagag gtgactgcag gagtggcaac cacctaggcc cggttagtgg 600
gatatatgta aagcccggcc ctgtctttta tcaggactac atgggcccag tctatcatag 660
agcccctcta gagtttttttg acgaagcaca gttttgtgag gtgaccaaaa ggataggtag 720
ggtgacaggt agtgacggaa agctttacca tatatacgtg tgcatcgatg gttgcatcct 780
gctgaagcta gccaagaggg gcgagccaag aaccctgaag tggattagaa atctcaccga 840
ctgtccattg tgggttacca gttgttctga tgatggtgca agtgcaagta aagagaagaa 900
accagatagg atcaacaagg gtaaattaaa gatagcccca aaagagcatg agaaggacag 960
caggactaag ccacctgatg ctacgattgt agtggaagga gtaaaatacc aggtcaaaaa 1020
gaaaggtaaa gttaagggaa agaataccca agacggcctg taccacaaca agaataaacc 1080
accagaatct aggaagaaat tagaaaaagc cctattggca tgggcagtga tagcaattat 1140
gttataccaa cctgttgcag ccgaaaatat aactcaatgg aacctgagtg acaacggtac 1200
caatggtatc cagcacgcta tgtaccttag aggagtcagc agaagcttgc atgggatctg 1260
gccagaaaaa atatgcaaag gagtccccac ctacctggcc acagacacgg aactgagaga 1320
aatacaggga atgatggatg ccagcgaggg gacaaactat acgtgctgta agttacagag 1380
acatgaatgg aacaaacatg gatggtgtaa ctggtataac atagacccct ggatacagtt 1440
gatgaataga acccaagcaa acttggcaga aggccctccg agcaaggagt gcgccgtgac 1500
ttgcaggtac gataaaaatg ctgacattaa cgtggtcacc caggccagaa acaggccaac 1560
caccctaact ggctgcaaga aagggaaaaa tttttctttt gcgggtacag ttatagaggg 1620
cccatgtaat ttcaacgttt ctgttgagga tatcttatat ggggatcatg agtgtggcag 1680
tctactccag gatacggctc tatacctagt agatggaatg accaacacta tagagagagc 1740
caggcaggga gccgcgaggg tgacatcttg gctagggagg caactcagaa ctgccgggaa 1800
gaggttggag ggcagaagca aaacctggtt tggtgcctat gccctatcac cttattgtaa 1860
tgtgacaagc aaaatagggt acatatggta cactaacaac tgtaccccgg cttgcctccc 1920
caaaaataca aagataatag gccccggtaa atttgacact aacgcggaag acggaaagat 1980
tctccatgag atggggggcc acctatcaga atttctgctg ctctctctgg tcgttctgtc 2040
tgacttcgcc cctgaaacag ccagcgcgtt atacctcatt ttgcactacg tgatccctca 2100

-continued

```
atcccatgaa gaacctgaag gctgtgacac aaaccagctg aatttaacag tggaactcag   2160
gactgaagac gtgataccat catcagtctg gaatgttggc aaatatgtgt gtgttagacc   2220
agactggtgg ccatatgaaa ccaaggtggc tttgttattt gaagaggcag gacaggtcgt   2280
aaagttagcc ttgcgggcac tgagggattt aaccagggtc tggaatagcg catcaaccac   2340
ggcattcctc atctgcttga taaaagtatt aagaggacag gtcgtgcaag gtgtgatatg   2400
gctgttactg gtaactgggg cacaaggccg gctagcctgc aaggaagatc acaggtacgc   2460
tatatcaaca accaatgaga tagggctact tggggccgaa ggtctcacta ccacctggaa   2520
agaatacaac cacaatttgc aactggatga tgggaccgtc aaggccatct gcatggcagg   2580
ttcctttaaa gtcacagcac ttaatgtggt tagtaggagg tatctggcat cattacataa   2640
ggacgcttta cccacttccg tgacattcga gctcctgttc gacgggacca gcccattgac   2700
cgaggaaatg ggagatgact tcgggttcgg actgtgtccg tatgatacga gccctgtagt   2760
caagggaaag tacaacacaa ccttgttgaa tggtagtgca ttctacctag tttgcccaat   2820
agggtggacg ggtgttatag agtgcacggc agtgagcccg acaactctga gaacagaagt   2880
ggtaaagacc ttcagaagag agaaaccctt tccgtacaga agggattgtg tgaccactac   2940
agtggaaaat gaagatctat tctactgtaa aacggggggc aatgatacat gtacgaaagg   3000
tgaaccagtg acctacacgg gggggccagt aaaacaatgc agatggtgtg gcttcgactt   3060
caatgagcct gacggactcc cacactaccc cataggtaag tgcattttgg caaatgagac   3120
aggttacaga atagtggatt caacggactg taacagagat ggcgttgtaa tcagcacaga   3180
ggggagtcat gagtgcttga ttggtaacac aactgtcaag gtgcatgcat tagatgaaag   3240
actaggccct atgccatgca ggcctaagga gatcgtctct agtgcgggac ctgtaaggaa   3300
aacttcctgt acattcaact acgcaaaaac tctgaggaac aggtattatg agcccaggga   3360
cagctatttc caacaatata tgctcaaggg cgagtatcag tactggtttg atctggatgt   3420
gaccgaccgc cactcagatt acttcgcaga attcattgtc ttggtggtgg tggcactgtt   3480
gggaggaaga tatgtcctgt ggctaatagt gacctacata gttctaacag aacaactcgc   3540
cgctggtcta cagttaggcc agggtgaggt agtgttaata gggaacttaa tcacccacac   3600
agatattgag gttgtagtat atttcttact gctctatttg gtcatgagag atgagcctat   3660
aaagaaatgg atactactgc tgttccatgc tatgaccaac aatccagtta agaccataac   3720
agtggcactg ctcatggtta gcggggttgc caagggtgga aagatagatg gtggttggca   3780
gcggctgccg gagaccaact ttgatatcca actcgcgctg acagttatag tagtcgctgt   3840
gatgttgctg gcaaagaaag atccgactac cgtccccttg gttataacgg tggcaaccct   3900
gagaacggct aagataacta atggacttag tacagatcta gccatagcta cagtgtcaac   3960
agctttgcta acctggacct acattagtga ctattataaa tacaagacct tgctacagta   4020
ccttattagc acagtgacag gtatcttctt gataagggta ctgaaggggg taggtgagtt   4080
agatttacac accccaacct taccatctta cagacccctc ttcttcatcc tcgtgtacct   4140
catttccact gcagtggtaa caagatggaa tctggacata gccggattgc tgctgcagtg   4200
tgtcccaacc cttttaatgg ttttcacgat gtgggcagac atccttaccc tgatcctcat   4260
actgcctact tacgagttga caaaactata ttacctcaag gaagtgaaga ttggggcaga   4320
aaggggctgg ttgtggaaga ccaacttcaa gagggtaaat gacatatacg aagttgacca   4380
agctggtgag gggtgtacct tttcccatc aaaacaaaag acaggtacaa taacaggtac   4440
```

-continued tatgttgcca ttgatcaaag ccatactcat aagttgcatc agcaataagt ggcaatttat 4500
atatctattg tacttgatat tcgaagtgtc ttactacctt cacaagaaga tcatagatga 4560
aatagcagga gggaccaact tcatctcgag acttgtagcc gctctgattg aagccaattg 4620
ggcctttgac aacgaagaag ttagaggttt aaagaagttc ttcctgctgt ctagtagggt 4680
taaagaactg atcatcaaac acaaagtgag gaatgaagtg atggtccact ggtttggcga 4740
cgaagaggtc tatgggatgc cgaagctggt tggcttagtc aaggcagcaa cactgagtaa 4800
aaataaacat tgtattttgt gcaccgtctg tgaaaacaga gagtggagag gagaaacctg 4860
cccaaaatgc ggccgttttg ggccaccagt gacctgtggc atgaccctag ccgactttga 4920
agaaaaacac tataagagga ttttctttag agaggatcaa tcagaagggc cggttaggga 4980
ggagtatgca gggtatctgc aatatagagc cagagggcaa ttattcctga ggaatctccc 5040
ggtgctagca acaaaagtca agatgctcct ggtcggaaat cttgggacgg aggtgggggga 5100 tttggaacac cttggctggg tgctcagagg gcctgccgtt tgcaagaagg ttaccgaaca 5160
tgagaaatgc accacatcca taatggacaa attaactgct ttcttcggtg ttatgccaag 5220
gggcaccaca cctagagccc ctgtgagatt ccccacctct ctcttaaaga taagaagggg 5280
gctggaaact ggctgggcgt acacacacca aggtggcatc agttcagtgg accatgtcac 5340
ttgtgggaaa gacttactgg tatgtgacac tatgggccgg acaagggttg tttgccaatc 5400
aaataacaag atgacagacg agtccgagta tggagttaaa actgactccg gatgcccgga 5460
gggagctagg tgttacgtgt tcaacccaga ggcagttaac atatccggga ctaaaggagc 5520
catggtccac ttacaaaaaa ctggaggaga attcacctgt gtgacagcat cagggactcc 5580
ggccttcttt gatctcaaga acctcaaagg ctggtcaggg ctgccgatat ttgaggcatc 5640
aagtggaaga gtagtcggca gggttaaggt cgggaagaat gaggactcta aaccaaccaa 5700
gcttatgagt ggaatacaaa cagtctccaa aagtaccaca gacttgacag aaatggtaaa 5760
gaaaataaca accatgaaca ggggagaatt cagacaaata acccttgcca caggtgccgg 5820
aaaaaccacg gaactcccta gatcagtcat agaagagata ggaaggcata agagggtctt 5880
ggtcttgatc cctctgaggg cggcagcaga gtcagtatac caatatatga gacaaaaaca 5940
cccaagcata gcattcaact tgaggatagg ggagatgaag gaaggggaca tggccacagg 6000
gataacctat gcctcatatg gttacttctg tcagatgcca caacctaagc tgcgagccgc 6060
gatggttgag tactccttca tattccttga tgagtaccac tgtgccaccc ccgaacaatt 6120
ggctatcatg ggaaagatcc acagattttc agagaacctg cgggtagtag ccatgaccgc 6180
aacaccagca ggcacggtaa caactacagg gcaaaaacac cctatagaag aatacatagc 6240
cccagaagtg atgaaggggg aagacttagg ttcagagtac ttggacatag ctggactaaa 6300
gataccagta gaggagatga agagtaacat gctggtcttt gtgcccacaa ggaacatggc 6360
tgtagagacg gcaaagaaac tgaaagctaa gggttataac tcaggctact attatagtgg 6420
agaggatcca tctaacctga gggtggtaac atcacagtcc ccgtacgtgg tggtagcaac 6480
caacgcaata gaatcaggtg ttactctccc agacttggat gtggtcgtcg acacagggct 6540
taagtgtgaa aagaggatac ggctgtcacc taagatgccc ttcatagtga cgggcctgaa 6600
gagaatggct gtcacgattg gggaacaagc ccagagaagg gggagagttg ggagagtgaa 6660
gcctgggaga tactacagga gtcaagaaac ccccgttggt tccaaagatt accattacga 6720
cctactgcaa gcacagaggt acggtataga agatgggata aacatcacca aatcttttag 6780
agagatgaat tatgattgga gcctttatga ggaggatagt ctgatgatta cacaattgga 6840

-continued aatcctcaac aatctgttga tatcagaaga gctaccaatg gcagtaaaaa atataatggc 6900
caggactgac cacccagaac caatccaact ggcgtacaac agctacgaaa cgcaggtgcc 6960
agtgctattc ccaaaaataa aaaatggaga ggtgactgac agttacgata actatacctt 7020
cctcaacgca agaaagctgg gggatgatgt acctccctac gtgtatgcca cagaggatga 7080
ggacttagcg gtagagctgc tgggcttaga ctggccggac cctgggaacc aaggaaccgt 7140
ggaggctggt agagcactaa aacaagtagt tggtctatca acagctgaga acgccctgtt 7200
agtagcttta ttcggctatg taggatatca ggcactctca aagaggcata taccagtagt 7260
cacagacata tattcaattg aagatcacag gttggaagac accacacacc tacagtatgc 7320
cccgaatgct atcaagacgg aggggaagga gacagaattg aaggagctag ctcaggggga 7380
tgtgcagaga tgtatggaag ctatgactaa ttatgcaaga gatggcatcc aattcatgaa 7440
gtctcaggca ctgaaagtga aagaaacccc cacttacaaa gagacaatgg acaccgtggc 7500
ggactatgta aagaagttca tggaggcact ggcggacagc aaagaagaca tcataaaata 7560
tgggttgtgg gggacgcaca caaccttata taagagcatc ggtgctaggc ttgggaacga 7620
gactgcgttc gctaccctgg tcgtgaaatg gctggcattt gggggagaat caatagcaga 7680
ccatgtcaaa caagcggcca cagacttggt cgtttactat atcatcaaca gacctcagtt 7740
cccaggagac acggagacac aacaggaagg aaggaaattt gtagccagcc tactggtctc 7800
agccctggct acttacactt acaaaagctg gaattacaat aatctgtcca agatagttga 7860
accggctttg gctactctgc cctatgccgc cacagctctc aagctattcg cccccactcg 7920
attggagagc gttgtcatac tgagtaccgc aatctacaaa acctacctat caatcaggcg 7980
cggaaaaagc gatggtttgc taggcacagg ggttagtgcg gctatggaaa tcatgtcaca 8040
aaacccagta tctgtgggta tagcggtcat gctaggggtg ggggccgtag cggcccacaa 8100
tgcaatcgaa gccagtgagc agaagagaac actactcatg aaagtttttg taaagaactt 8160
cttggatcag gcagccactg atgaattagt caaggagagc cctgagaaaa taataatggc 8220
tttgtttgaa gcagtgcaga cagtcggcaa ccctcttaga ctggtatacc acctttacgg 8280
agttttttac aaagggtggg aggcaaaaga gttggcccaa aggacagccg gtaggaatct 8340
tttcactttg ataatgtttg aggctgtgga actactggga gtagatagcg aaggaaagat 8400
ccgccagcta tcaagcaatt acatactaga gctcctgtat aagttccgtg acagtatcaa 8460
gtccagcgtg aggcagatgg caatcagctg ggcccctgcc ccttttagtt gtgattggac 8520
accgacggat gacagaatag ggcttcccca agataatttc ctccgagtgg agacaaaatg 8580
cccctgtggt tacaagatga aagcagttaa gaattgtgct ggggagttga gactcttaga 8640
agaggaaggc tcatttctct gcaggaataa attcgggaga ggttcacgga actacagggt 8700
gacaaaatac tatgatgaca atctatcaga aataaagcca gtgataagaa tggaaggaca 8760
tgtggaactc tactacaagg gagccactat taaactggat ttcaacaaca gtaaaacaat 8820
attggcaacc gataaatggg aggtcgatca ctccactctg gtcagggtgc tcaagaggca 8880
cacaggggct ggatatcgtg gggcatacct gggtgagaaa ccgaaccaca aacatctgat 8940
agagagggac tgcgcaacca tcaccaaaga taaggtttgt ttctcaaga tgaagagagg 9000
gtgtgcattt acttatgact tatcccttca caaccttacc cggctgatcg aattggtaca 9060
caagaataac ttggaagaca aagagattcc tgccgttacg gtcacaacct ggctggctta 9120
cacatttgta aatgaagata tagggaccat aaaaccagcc ttcggggaga aaataacacc 9180

-continued

```
agagatgcag gaggagataa ccttgcagcc tgctgtagtg gtggatgcaa ctgacgtgac   9240
cgtgaccgtg gtaggggaaa cccctactat gactacaggg gagaccccaa caacgttcac   9300
cagctcaggt ccagacccga aaggccaaca agttttaaaa ctgggagtag gtgaaggcca   9360
ataccccggg actaatccac agagagcaag cctgcacgaa gccatacaaa gcgcagatga   9420
aaggccctct gtgttgatat tggggtctga taaagccacc tctaatagag tgaaaactgt   9480
aaagaatgtg aaggtataca gaggcaggga cccactagaa gtgagagata tgatgaggag   9540
gggaaagatc ctagtcatag ccctgtctag ggttgataat gctctattga aatttgtaga   9600
ttacaaaggc acctttctaa ctagagagac cctggaggca ttaagtttgg gtaggccaaa   9660
aaagaaaaac ataaccaagg cagaagcaca gtggttgctg cgcctcgaag accaaatgga   9720
agagctaccc gattggttcg cagccgggga acccattttt ttagaggcca atattaaaca   9780
tgacaggtat catctggtag gggatatagc tactatcaaa gagaaagcca aacaattggg   9840
ggctacagac tctacaaaga tatccaagga ggttggtgca aaagtatatt ctatgaaatt   9900
gagtaattgg gtgatgcaag aagaaaacaa acagagcaac ttgacccccct tatttgaaga   9960
gctcctacag cagtgtccac ccggaggcca aaacaaaact gcacatatgg tctctgctta  10020
ccaactagct caagggaact ggatgccaac cagctgccat gtttttatgg ggaccatatc  10080
tgccagaagg actaagaccc atccatatga agcatatgtc aagttaaggg agttggtaga  10140
ggaacacaag atgaaaacat tgtgtcccgg atcaagtctg cgtaagcaca atgaatgggt  10200
aattggcaag atcaaatacc agggcaacct gaggaccaaa cacatgttga accccggcaa  10260
ggtggcagag caactgcaca gagaaggaca cagacacaat gtgtataaca agacaatagg  10320
ctcagtgatg acagctactg gcatcaggtt ggagaagttg cccgtggtta gggcccagac  10380
agacacaacc aacttccacc aagcaataag ggataagata gacaaggaag agaatctaca  10440
gaccccgggt ttacataaga aactaatgga agttttcaat gcattgaaac gacccgagtt  10500
agagtcctcc tatgacgctg tggaatggga ggaattggag agaggaataa acagaaaggg  10560
tgctgctggt ttctttgaac gcaaaaacat aggggagata ttggattcag agaaaaataa  10620
agtagaagag attattgaca atctgaaaaa gggtagaaat atcaaatact atgaaaccgc  10680
aatcccaaaa aatgaaaaga gggatgtcaa tgatgactgg accgcaggtg actttgtgga  10740
cgagaagaaa cccagagtca tacaataccc tgaagcaaaa acaaggctgg ccatcaccaa  10800
ggtgatgtat aagtgggtga agcagaagcc agtagtcata cccgggtatg aagggaagac  10860
acctctgttc caaatttttg acaaagtaaa gaaggaatgg gatcaattcc aaaatccagt  10920
ggcagtgagc ttcgacacta aggcgtggga cacccaggtg accacaaatg atctggagct  10980
gataaaggac atacaaaagt actacttcaa gaagaaatgg cataaattta ttgacaccct  11040
gactatgcat atgtcagaag tacccgtaat cactgctgat ggggaggtgt atataaggaa  11100
agggcaaaga ggtagtggac agcccgacac aagcgcaggc aacagcatgc taaatgtgtt  11160
aacaatggtt tatgccttct gcgaggccac aggggtaccc tacaagagtt ttgacagggt  11220
ggcaaaaatt catgtgtgcg gggacgatgg tttcctgatc acagagagag ctctcggcga  11280
gaaattcgca agcaagggag tccaaatcct gtatgaagct gggaagcccc agaagatcac  11340
tgaaggggac aaaatgaaag tggcctacca atttgatgat attgagtttt gctcccatac  11400
accaatacaa gtaaggtggt cagataacac ttctagctac atgccaggga gaaatacaac  11460
cacaatcctg gctaaaatgg ccacaaggtt agattccagt ggtgagaggg gtaccatagc  11520
gtacgagaaa gcagtagcat tcagcttcct gctaatgtat tcctggaacc cactaatcag  11580
```

```
aaggatttgc ttattggtac tatcaactga actgcaagtg aaaccaggga agtcaaccac  11640

ttactattat gaaggggacc cgatatctgc ctacaaggaa gtcatcggcc acaatctttt  11700

cgatctcaag agaacaagct tcgagaagct ggccaagtta aatctcagca tgtccgtact  11760

cggggcctgg actagacaca ccagcaaaag actactacaa gactgtgtca atatgggtgt  11820

taaagagggc aactggttag tcaatgcaga cagactggtg agtagtaaga ctggaaatag  11880

gtatgtacct ggagaaggcc acaccctgca agggagacat tatgaagaac tggtgttggc  11940

aagaaaacag atcaacagct tccaagggac agacaggtac aatctaggcc caatagtcaa  12000

catggtgtta aggaggctga gagtcatgat gatgaccctg atagggagag ggtatgagt  12060

gcgggtgacc cgcgatctgg acccgtcagt aggaccctat tgtagataac actaattttt  12120

tatttattta gatattacta tttatttatt tatttattta ttgaatgagt aagaactggt  12180

acaaactacc tcatgttacc acactacact cattttaaca gcactttagc tggaaggaaa  12240

attcctgacg tccacagttg gactaaggta atttcctaac ggccc                  12285
```

<210> SEQ ID NO 2
<211> LENGTH: 3898
<212> TYPE: PRT
<213> ORGANISM: Classical Swine Fever Virus

<400> SEQUENCE: 2

```
Met Glu Leu Asn His Phe Glu Leu Leu Tyr Lys Thr Asn Lys Gln Lys
1               5                   10                  15

Pro Met Gly Val Glu Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Leu Thr Asp
145                 150                 155                 160

Cys Pro Leu Trp Val Thr Ser Cys Ser Asp Asp Gly Ala Ser Ala Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Lys Pro Pro Asp Ala Thr
        195                 200                 205

Ile Val Val Glu Gly Val Lys Tyr Gln Val Lys Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
```

-continued

```
                245                 250                 255

Ile Ala Ile Met Leu Tyr Gln Pro Val Ala Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Ser Arg Ser Leu His Gly Ile Trp Pro Glu Lys Ile
    290                 295                 300

Cys Lys Gly Val Pro Thr Tyr Leu Ala Thr Asp Thr Glu Leu Arg Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Ala Asn Leu
        355                 360                 365

Ala Glu Gly Pro Pro Ser Lys Glu Cys Ala Val Thr Cys Arg Tyr Asp
    370                 375                 380

Lys Asn Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
            420                 425                 430

Tyr Gly Asp His Glu Cys Gly Ser Leu Leu Gln Asp Thr Ala Leu Tyr
        435                 440                 445

Leu Val Asp Gly Met Thr Asn Thr Ile Glu Arg Ala Arg Gln Gly Ala
    450                 455                 460

Ala Arg Val Thr Ser Trp Leu Gly Arg Gln Leu Arg Thr Ala Gly Lys
465                 470                 475                 480

Arg Leu Glu Gly Arg Ser Lys Thr Trp Phe Gly Ala Tyr Ala Leu Ser
                485                 490                 495

Pro Tyr Cys Asn Val Thr Ser Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Val Leu Ser
545                 550                 555                 560

Asp Phe Ala Pro Glu Thr Ala Ser Ala Leu Tyr Leu Ile Leu His Tyr
                565                 570                 575

Val Ile Pro Gln Ser His Glu Glu Pro Glu Gly Cys Asp Thr Asn Gln
            580                 585                 590

Leu Asn Leu Thr Val Glu Leu Arg Thr Glu Asp Val Ile Pro Ser Ser
        595                 600                 605

Val Trp Asn Val Gly Lys Tyr Val Cys Val Arg Pro Asp Trp Trp Pro
    610                 615                 620

Tyr Glu Thr Lys Val Ala Leu Leu Phe Glu Glu Ala Gly Gln Val Val
625                 630                 635                 640

Lys Leu Ala Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
            660                 665                 670
```

```
Gln Val Val Gln Gly Val Ile Trp Leu Leu Leu Val Thr Gly Ala Gln
        675                 680                 685

Gly Arg Leu Ala Cys Lys Glu Asp His Arg Tyr Ala Ile Ser Thr Thr
    690                 695                 700

Asn Glu Ile Gly Leu Leu Gly Ala Glu Gly Leu Thr Thr Thr Trp Lys
705                 710                 715                 720

Glu Tyr Asn His Asn Leu Gln Leu Asp Asp Gly Thr Val Lys Ala Ile
                725                 730                 735

Cys Met Ala Gly Ser Phe Lys Val Thr Ala Leu Asn Val Val Ser Arg
            740                 745                 750

Arg Tyr Leu Ala Ser Leu His Lys Asp Ala Leu Pro Thr Ser Val Thr
        755                 760                 765

Phe Glu Leu Leu Phe Asp Gly Thr Ser Pro Leu Thr Glu Glu Met Gly
    770                 775                 780

Asp Asp Phe Gly Phe Gly Leu Cys Pro Tyr Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Glu Lys
        835                 840                 845

Pro Phe Pro Tyr Arg Arg Asp Cys Val Thr Thr Thr Val Glu Asn Glu
    850                 855                 860

Asp Leu Phe Tyr Cys Lys Thr Gly Gly Asn Asp Thr Cys Thr Lys Gly
865                 870                 875                 880

Glu Pro Val Thr Tyr Thr Gly Gly Pro Val Lys Gln Cys Arg Trp Cys
                885                 890                 895

Gly Phe Asp Phe Asn Glu Pro Asp Gly Leu Pro His Tyr Pro Ile Gly
            900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
    930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Ala Gly
                965                 970                 975

Pro Val Arg Lys Thr Ser Cys Thr Phe Asn Tyr Ala Lys Thr Leu Arg
            980                 985                 990

Asn Arg Tyr Tyr Glu Pro Arg Asp  Ser Tyr Phe Gln Gln  Tyr Met Leu
        995                 1000                1005

Lys Gly  Glu Tyr Gln Tyr Trp  Phe Asp Leu Asp Val  Thr Asp Arg
    1010                1015                1020

His Ser  Asp Tyr Phe Ala Glu  Phe Ile Val Leu Val  Val Val Ala
    1025                1030                1035

Leu Leu  Gly Gly Arg Tyr Val  Leu Trp Leu Ile Val  Thr Tyr Ile
    1040                1045                1050

Val Leu  Thr Glu Gln Leu Ala  Ala Gly Leu Gln Leu  Gly Gln Gly
    1055                1060                1065

Glu Val  Val Leu Ile Gly Asn  Leu Ile Thr His Thr  Asp Ile Glu
    1070                1075                1080
```

-continued

Val Val Val Tyr Phe Leu Leu Leu Tyr Leu Val Met Arg Asp Glu
1085 1090 1095

Pro Ile Lys Lys Trp Ile Leu Leu Leu Phe His Ala Met Thr Asn
1100 1105 1110

Asn Pro Val Lys Thr Ile Thr Val Ala Leu Leu Met Val Ser Gly
1115 1120 1125

Val Ala Lys Gly Gly Lys Ile Asp Gly Gly Trp Gln Arg Leu Pro
1130 1135 1140

Glu Thr Asn Phe Asp Ile Gln Leu Ala Leu Thr Val Ile Val Val
1145 1150 1155

Ala Val Met Leu Leu Ala Lys Lys Asp Pro Thr Thr Val Pro Leu
1160 1165 1170

Val Ile Thr Val Ala Thr Leu Arg Thr Ala Lys Ile Thr Asn Gly
1175 1180 1185

Leu Ser Thr Asp Leu Ala Ile Ala Thr Val Ser Thr Ala Leu Leu
1190 1195 1200

Thr Trp Thr Tyr Ile Ser Asp Tyr Tyr Lys Tyr Lys Thr Leu Leu
1205 1210 1215

Gln Tyr Leu Ile Ser Thr Val Thr Gly Ile Phe Leu Ile Arg Val
1220 1225 1230

Leu Lys Gly Val Gly Glu Leu Asp Leu His Thr Pro Thr Leu Pro
1235 1240 1245

Ser Tyr Arg Pro Leu Phe Phe Ile Leu Val Tyr Leu Ile Ser Thr
1250 1255 1260

Ala Val Val Thr Arg Trp Asn Leu Asp Ile Ala Gly Leu Leu Leu
1265 1270 1275

Gln Cys Val Pro Thr Leu Leu Met Val Phe Thr Met Trp Ala Asp
1280 1285 1290

Ile Leu Thr Leu Ile Leu Ile Leu Pro Thr Tyr Glu Leu Thr Lys
1295 1300 1305

Leu Tyr Tyr Leu Lys Glu Val Lys Ile Gly Ala Glu Arg Gly Trp
1310 1315 1320

Leu Trp Lys Thr Asn Phe Lys Arg Val Asn Asp Ile Tyr Glu Val
1325 1330 1335

Asp Gln Ala Gly Glu Gly Val Tyr Leu Phe Pro Ser Lys Gln Lys
1340 1345 1350

Thr Gly Thr Ile Thr Gly Thr Met Leu Pro Leu Ile Lys Ala Ile
1355 1360 1365

Leu Ile Ser Cys Ile Ser Asn Lys Trp Gln Phe Ile Tyr Leu Leu
1370 1375 1380

Tyr Leu Ile Phe Glu Val Ser Tyr Tyr Leu His Lys Lys Ile Ile
1385 1390 1395

Asp Glu Ile Ala Gly Gly Thr Asn Phe Ile Ser Arg Leu Val Ala
1400 1405 1410

Ala Leu Ile Glu Ala Asn Trp Ala Phe Asp Asn Glu Glu Val Arg
1415 1420 1425

Gly Leu Lys Lys Phe Phe Leu Leu Ser Ser Arg Val Lys Glu Leu
1430 1435 1440

Ile Ile Lys His Lys Val Arg Asn Glu Val Met Val His Trp Phe
1445 1450 1455

Gly Asp Glu Glu Val Tyr Gly Met Pro Lys Leu Val Gly Leu Val
1460 1465 1470

Lys Ala Ala Thr Leu Ser Lys Asn Lys His Cys Ile Leu Cys Thr

-continued

```
    1475                1480                1485

Val Cys  Glu Asn Arg Glu Trp  Arg Gly Glu Thr Cys  Pro Lys Cys
    1490                1495                1500

Gly Arg  Phe Gly Pro Pro Val  Thr Cys Gly Met Thr  Leu Ala Asp
    1505                1510                1515

Phe Glu  Glu Lys His Tyr Lys  Arg Ile Phe Phe Arg  Glu Asp Gln
    1520                1525                1530

Ser Glu  Gly Pro Val Arg Glu  Glu Tyr Ala Gly Tyr  Leu Gln Tyr
    1535                1540                1545

Arg Ala  Arg Gly Gln Leu Phe  Leu Arg Asn Leu Pro  Val Leu Ala
    1550                1555                1560

Thr Lys  Val Lys Met Leu Leu  Val Gly Asn Leu Gly  Thr Glu Val
    1565                1570                1575

Gly Asp  Leu Glu His Leu Gly  Trp Val Leu Arg Gly  Pro Ala Val
    1580                1585                1590

Cys Lys  Lys Val Thr Glu His  Glu Lys Cys Thr Thr  Ser Ile Met
    1595                1600                1605

Asp Lys  Leu Thr Ala Phe Phe  Gly Val Met Pro Arg  Gly Thr Thr
    1610                1615                1620

Pro Arg  Ala Pro Val Arg Phe  Pro Thr Ser Leu Leu  Lys Ile Arg
    1625                1630                1635

Arg Gly  Leu Glu Thr Gly Trp  Ala Tyr Thr His Gln  Gly Gly Ile
    1640                1645                1650

Ser Ser  Val Asp His Val Thr  Cys Gly Lys Asp Leu  Leu Val Cys
    1655                1660                1665

Asp Thr  Met Gly Arg Thr Arg  Val Val Cys Gln Ser  Asn Asn Lys
    1670                1675                1680

Met Thr  Asp Glu Ser Glu Tyr  Gly Val Lys Thr Asp  Ser Gly Cys
    1685                1690                1695

Pro Glu  Gly Ala Arg Cys Tyr  Val Phe Asn Pro Glu  Ala Val Asn
    1700                1705                1710

Ile Ser  Gly Thr Lys Gly Ala  Met Val His Leu Gln  Lys Thr Gly
    1715                1720                1725

Gly Glu  Phe Thr Cys Val Thr  Ala Ser Gly Thr Pro  Ala Phe Phe
    1730                1735                1740

Asp Leu  Lys Asn Leu Lys Gly  Trp Ser Gly Leu Pro  Ile Phe Glu
    1745                1750                1755

Ala Ser  Ser Gly Arg Val Val  Gly Arg Val Lys Val  Gly Lys Asn
    1760                1765                1770

Glu Asp  Ser Lys Pro Thr Lys  Leu Met Ser Gly Ile  Gln Thr Val
    1775                1780                1785

Ser Lys  Ser Thr Thr Asp Leu  Thr Glu Met Val Lys  Lys Ile Thr
    1790                1795                1800

Thr Met  Asn Arg Gly Glu Phe  Arg Gln Ile Thr Leu  Ala Thr Gly
    1805                1810                1815

Ala Gly  Lys Thr Thr Glu Leu  Pro Arg Ser Val Ile  Glu Glu Ile
    1820                1825                1830

Gly Arg  His Lys Arg Val Leu  Val Leu Ile Pro Leu  Arg Ala Ala
    1835                1840                1845

Ala Glu  Ser Val Tyr Gln Tyr  Met Arg Gln Lys His  Pro Ser Ile
    1850                1855                1860

Ala Phe  Asn Leu Arg Ile Gly  Glu Met Lys Glu Gly  Asp Met Ala
    1865                1870                1875
```

-continued

```
Thr Gly  Ile Thr Tyr Ala Ser  Tyr Gly Tyr Phe Cys  Gln Met Pro
    1880                 1885                 1890

Gln Pro  Lys Leu Arg Ala Ala  Met Val Glu Tyr Ser  Phe Ile Phe
    1895                 1900                 1905

Leu Asp  Glu Tyr His Cys Ala  Thr Pro Glu Gln Leu  Ala Ile Met
    1910                 1915                 1920

Gly Lys  Ile His Arg Phe Ser  Glu Asn Leu Arg Val  Val Ala Met
    1925                 1930                 1935

Thr Ala  Thr Pro Ala Gly Thr  Val Thr Thr Thr Gly  Gln Lys His
    1940                 1945                 1950

Pro Ile  Glu Glu Tyr Ile Ala  Pro Glu Val Met Lys  Gly Glu Asp
    1955                 1960                 1965

Leu Gly  Ser Glu Tyr Leu Asp  Ile Ala Gly Leu Lys  Ile Pro Val
    1970                 1975                 1980

Glu Glu  Met Lys Ser Asn Met  Leu Val Phe Val Pro  Thr Arg Asn
    1985                 1990                 1995

Met Ala  Val Glu Thr Ala Lys  Lys Leu Lys Ala Lys  Gly Tyr Asn
    2000                 2005                 2010

Ser Gly  Tyr Tyr Tyr Ser Gly  Glu Asp Pro Ser Asn  Leu Arg Val
    2015                 2020                 2025

Val Thr  Ser Gln Ser Pro Tyr  Val Val Val Ala Thr  Asn Ala Ile
    2030                 2035                 2040

Glu Ser  Gly Val Thr Leu Pro  Asp Leu Asp Val Val  Val Asp Thr
    2045                 2050                 2055

Gly Leu  Lys Cys Glu Lys Arg  Ile Arg Leu Ser Pro  Lys Met Pro
    2060                 2065                 2070

Phe Ile  Val Thr Gly Leu Lys  Arg Met Ala Val Thr  Ile Gly Glu
    2075                 2080                 2085

Gln Ala  Gln Arg Arg Gly Arg  Val Gly Arg Val Lys  Pro Gly Arg
    2090                 2095                 2100

Tyr Tyr  Arg Ser Gln Glu Thr  Pro Val Gly Ser Lys  Asp Tyr His
    2105                 2110                 2115

Tyr Asp  Leu Leu Gln Ala Gln  Arg Tyr Gly Ile Glu  Asp Gly Ile
    2120                 2125                 2130

Asn Ile  Thr Lys Ser Phe Arg  Glu Met Asn Tyr Asp  Trp Ser Leu
    2135                 2140                 2145

Tyr Glu  Glu Asp Ser Leu Met  Ile Thr Gln Leu Glu  Ile Leu Asn
    2150                 2155                 2160

Asn Leu  Leu Ile Ser Glu Glu  Leu Pro Met Ala Val  Lys Asn Ile
    2165                 2170                 2175

Met Ala  Arg Thr Asp His Pro  Glu Pro Ile Gln Leu  Ala Tyr Asn
    2180                 2185                 2190

Ser Tyr  Glu Thr Gln Val Pro  Val Leu Phe Pro Lys  Ile Lys Asn
    2195                 2200                 2205

Gly Glu  Val Thr Asp Ser Tyr  Asp Asn Tyr Thr Phe  Leu Asn Ala
    2210                 2215                 2220

Arg Lys  Leu Gly Asp Asp Val  Pro Pro Tyr Val Tyr  Ala Thr Glu
    2225                 2230                 2235

Asp Glu  Asp Leu Ala Val Glu  Leu Leu Gly Leu Asp  Trp Pro Asp
    2240                 2245                 2250

Pro Gly  Asn Gln Gly Thr Val  Glu Ala Gly Arg Ala  Leu Lys Gln
    2255                 2260                 2265
```

-continued

```
Val Val  Gly Leu Ser Thr Ala  Glu Asn Ala Leu Leu  Val Ala Leu
    2270                 2275                 2280

Phe Gly  Tyr Val Gly Tyr Gln  Ala Leu Ser Lys Arg  His Ile Pro
    2285                 2290                 2295

Val Val  Thr Asp Ile Tyr Ser  Ile Glu Asp His Arg  Leu Glu Asp
    2300                 2305                 2310

Thr Thr  His Leu Gln Tyr Ala  Pro Asn Ala Ile Lys  Thr Glu Gly
    2315                 2320                 2325

Lys Glu  Thr Glu Leu Lys Glu  Leu Ala Gln Gly Asp  Val Gln Arg
    2330                 2335                 2340

Cys Met  Glu Ala Met Thr Asn  Tyr Ala Arg Asp Gly  Ile Gln Phe
    2345                 2350                 2355

Met Lys  Ser Gln Ala Leu Lys  Val Lys Glu Thr Pro  Thr Tyr Lys
    2360                 2365                 2370

Glu Thr  Met Asp Thr Val Ala  Asp Tyr Val Lys Lys  Phe Met Glu
    2375                 2380                 2385

Ala Leu  Ala Asp Ser Lys Glu  Asp Ile Ile Lys Tyr  Gly Leu Trp
    2390                 2395                 2400

Gly Thr  His Thr Thr Leu Tyr  Lys Ser Ile Gly Ala  Arg Leu Gly
    2405                 2410                 2415

Asn Glu  Thr Ala Phe Ala Thr  Leu Val Val Lys Trp  Leu Ala Phe
    2420                 2425                 2430

Gly Gly  Glu Ser Ile Ala Asp  His Val Lys Gln Ala  Ala Thr Asp
    2435                 2440                 2445

Leu Val  Val Tyr Tyr Ile Ile  Asn Arg Pro Gln Phe  Pro Gly Asp
    2450                 2455                 2460

Thr Glu  Thr Gln Gln Glu Gly  Arg Lys Phe Val Ala  Ser Leu Leu
    2465                 2470                 2475

Val Ser  Ala Leu Ala Thr Tyr  Thr Tyr Lys Ser Trp  Asn Tyr Asn
    2480                 2485                 2490

Asn Leu  Ser Lys Ile Val Glu  Pro Ala Leu Ala Thr  Leu Pro Tyr
    2495                 2500                 2505

Ala Ala  Thr Ala Leu Lys Leu  Phe Ala Pro Thr Arg  Leu Glu Ser
    2510                 2515                 2520

Val Val  Ile Leu Ser Thr Ala  Ile Tyr Lys Thr Tyr  Leu Ser Ile
    2525                 2530                 2535

Arg Arg  Gly Lys Ser Asp Gly  Leu Leu Gly Thr Gly  Val Ser Ala
    2540                 2545                 2550

Ala Met  Glu Ile Met Ser Gln  Asn Pro Val Ser Val  Gly Ile Ala
    2555                 2560                 2565

Val Met  Leu Gly Val Gly Ala  Val Ala Ala His Asn  Ala Ile Glu
    2570                 2575                 2580

Ala Ser  Glu Gln Lys Arg Thr  Leu Leu Met Lys Val  Phe Val Lys
    2585                 2590                 2595

Asn Phe  Leu Asp Gln Ala Ala  Thr Asp Glu Leu Val  Lys Glu Ser
    2600                 2605                 2610

Pro Glu  Lys Ile Ile Met Ala  Leu Phe Glu Ala Val  Gln Thr Val
    2615                 2620                 2625

Gly Asn  Pro Leu Arg Leu Val  Tyr His Leu Tyr Gly  Val Phe Tyr
    2630                 2635                 2640

Lys Gly  Trp Glu Ala Lys Glu  Leu Ala Gln Arg Thr  Ala Gly Arg
    2645                 2650                 2655

Asn Leu  Phe Thr Leu Ile Met  Phe Glu Ala Val Glu  Leu Leu Gly
```

```
    2660                2665                2670

Val Asp  Ser Glu Gly Lys Ile  Arg Gln Leu Ser Ser  Asn Tyr Ile
    2675                2680                2685

Leu Glu  Leu Leu Tyr Lys Phe  Arg Asp Ser Ile Lys  Ser Ser Val
    2690                2695                2700

Arg Gln  Met Ala Ile Ser Trp  Ala Pro Ala Pro Phe  Ser Cys Asp
    2705                2710                2715

Trp Thr  Pro Thr Asp Asp Arg  Ile Gly Leu Pro Gln  Asp Asn Phe
    2720                2725                2730

Leu Arg  Val Glu Thr Lys Cys  Pro Cys Gly Tyr Lys  Met Lys Ala
    2735                2740                2745

Val Lys  Asn Cys Ala Gly Glu  Leu Arg Leu Leu Glu  Glu Glu Gly
    2750                2755                2760

Ser Phe  Leu Cys Arg Asn Lys  Phe Gly Arg Gly Ser  Arg Asn Tyr
    2765                2770                2775

Arg Val  Thr Lys Tyr Tyr Asp  Asp Asn Leu Ser Glu  Ile Lys Pro
    2780                2785                2790

Val Ile  Arg Met Glu Gly His  Val Glu Leu Tyr Tyr  Lys Gly Ala
    2795                2800                2805

Thr Ile  Lys Leu Asp Phe Asn  Asn Ser Lys Thr Ile  Leu Ala Thr
    2810                2815                2820

Asp Lys  Trp Glu Val Asp His  Ser Thr Leu Val Arg  Val Leu Lys
    2825                2830                2835

Arg His  Thr Gly Ala Gly Tyr  Arg Gly Ala Tyr Leu  Gly Glu Lys
    2840                2845                2850

Pro Asn  His Lys His Leu Ile  Glu Arg Asp Cys Ala  Thr Ile Thr
    2855                2860                2865

Lys Asp  Lys Val Cys Phe Leu  Lys Met Lys Arg Gly  Cys Ala Phe
    2870                2875                2880

Thr Tyr  Asp Leu Ser Leu His  Asn Leu Thr Arg Leu  Ile Glu Leu
    2885                2890                2895

Val His  Lys Asn Asn Leu Glu  Asp Lys Glu Ile Pro  Ala Val Thr
    2900                2905                2910

Val Thr  Thr Trp Leu Ala Tyr  Thr Phe Val Asn Glu  Asp Ile Gly
    2915                2920                2925

Thr Ile  Lys Pro Ala Phe Gly  Glu Lys Ile Thr Pro  Glu Met Gln
    2930                2935                2940

Glu Glu  Ile Thr Leu Gln Pro  Ala Val Val Val Asp  Ala Thr Asp
    2945                2950                2955

Val Thr  Val Thr Val Val Gly  Glu Thr Pro Thr Met  Thr Thr Gly
    2960                2965                2970

Glu Thr  Pro Thr Thr Phe Thr  Ser Ser Gly Pro Asp  Pro Lys Gly
    2975                2980                2985

Gln Gln  Val Leu Lys Leu Gly  Val Gly Glu Gly Gln  Tyr Pro Gly
    2990                2995                3000

Thr Asn  Pro Gln Arg Ala Ser  Leu His Glu Ala Ile  Gln Ser Ala
    3005                3010                3015

Asp Glu  Arg Pro Ser Val Leu  Ile Leu Gly Ser Asp  Lys Ala Thr
    3020                3025                3030

Ser Asn  Arg Val Lys Thr Val  Lys Asn Val Lys Val  Tyr Arg Gly
    3035                3040                3045

Arg Asp  Pro Leu Glu Val Arg  Asp Met Met Arg Arg  Gly Lys Ile
    3050                3055                3060
```

-continued

```
Leu Val  Ile Ala Leu Ser Arg  Val Asp Asn Ala Leu  Leu Lys Phe
    3065                 3070                 3075

Val Asp  Tyr Lys Gly Thr Phe  Leu Thr Arg Glu Thr  Leu Glu Ala
    3080                 3085                 3090

Leu Ser  Leu Gly Arg Pro Lys  Lys Lys Asn Ile Thr  Lys Ala Glu
    3095                 3100                 3105

Ala Gln  Trp Leu Leu Arg Leu  Glu Asp Gln Met Glu  Glu Leu Pro
    3110                 3115                 3120

Asp Trp  Phe Ala Ala Gly Glu  Pro Ile Phe Leu Glu  Ala Asn Ile
    3125                 3130                 3135

Lys His  Asp Arg Tyr His Leu  Val Gly Asp Ile Ala  Thr Ile Lys
    3140                 3145                 3150

Glu Lys  Ala Lys Gln Leu Gly  Ala Thr Asp Ser Thr  Lys Ile Ser
    3155                 3160                 3165

Lys Glu  Val Gly Ala Lys Val  Tyr Ser Met Lys Leu  Ser Asn Trp
    3170                 3175                 3180

Val Met  Gln Glu Glu Asn Lys  Gln Ser Asn Leu Thr  Pro Leu Phe
    3185                 3190                 3195

Glu Glu  Leu Leu Gln Gln Cys  Pro Pro Gly Gly Gln  Asn Lys Thr
    3200                 3205                 3210

Ala His  Met Val Ser Ala Tyr  Gln Leu Ala Gln Gly  Asn Trp Met
    3215                 3220                 3225

Pro Thr  Ser Cys His Val Phe  Met Gly Thr Ile Ser  Ala Arg Arg
    3230                 3235                 3240

Thr Lys  Thr His Pro Tyr Glu  Ala Tyr Val Lys Leu  Arg Glu Leu
    3245                 3250                 3255

Val Glu  Glu His Lys Met Lys  Thr Leu Cys Pro Gly  Ser Ser Leu
    3260                 3265                 3270

Arg Lys  His Asn Glu Trp Val  Ile Gly Lys Ile Lys  Tyr Gln Gly
    3275                 3280                 3285

Asn Leu  Arg Thr Lys His Met  Leu Asn Pro Gly Lys  Val Ala Glu
    3290                 3295                 3300

Gln Leu  His Arg Glu Gly His  Arg His Asn Val Tyr  Asn Lys Thr
    3305                 3310                 3315

Ile Gly  Ser Val Met Thr Ala  Thr Gly Ile Arg Leu  Glu Lys Leu
    3320                 3325                 3330

Pro Val  Val Arg Ala Gln Thr  Asp Thr Thr Asn Phe  His Gln Ala
    3335                 3340                 3345

Ile Arg  Asp Lys Ile Asp Lys  Glu Glu Asn Leu Gln  Thr Pro Gly
    3350                 3355                 3360

Leu His  Lys Lys Leu Met Glu  Val Phe Asn Ala Leu  Lys Arg Pro
    3365                 3370                 3375

Glu Leu  Glu Ser Ser Tyr Asp  Ala Val Glu Trp Glu  Glu Leu Glu
    3380                 3385                 3390

Arg Gly  Ile Asn Arg Lys Gly  Ala Ala Gly Phe Phe  Glu Arg Lys
    3395                 3400                 3405

Asn Ile  Gly Glu Ile Leu Asp  Ser Glu Lys Asn Lys  Val Glu Glu
    3410                 3415                 3420

Ile Ile  Asp Asn Leu Lys Lys  Gly Arg Asn Ile Lys  Tyr Tyr Glu
    3425                 3430                 3435

Thr Ala  Ile Pro Lys Asn Glu  Lys Arg Asp Val Asn  Asp Asp Trp
    3440                 3445                 3450
```

-continued

```
Thr Ala  Gly Asp Phe Val Asp  Glu Lys Lys Pro Arg  Val Ile Gln
    3455                 3460                 3465

Tyr Pro  Glu Ala Lys Thr Arg  Leu Ala Ile Thr Lys  Val Met Tyr
    3470                 3475                 3480

Lys Trp  Val Lys Gln Lys Pro  Val Val Ile Pro Gly  Tyr Glu Gly
    3485                 3490                 3495

Lys Thr  Pro Leu Phe Gln Ile  Phe Asp Lys Val Lys  Lys Glu Trp
    3500                 3505                 3510

Asp Gln  Phe Gln Asn Pro Val  Ala Val Ser Phe Asp  Thr Lys Ala
    3515                 3520                 3525

Trp Asp  Thr Gln Val Thr Thr  Asn Asp Leu Glu Leu  Ile Lys Asp
    3530                 3535                 3540

Ile Gln  Lys Tyr Tyr Phe Lys  Lys Lys Trp His Lys  Phe Ile Asp
    3545                 3550                 3555

Thr Leu  Thr Met His Met Ser  Glu Val Pro Val Ile  Thr Ala Asp
    3560                 3565                 3570

Gly Glu  Val Tyr Ile Arg Lys  Gly Gln Arg Gly Ser  Gly Gln Pro
    3575                 3580                 3585

Asp Thr  Ser Ala Gly Asn Ser  Met Leu Asn Val Leu  Thr Met Val
    3590                 3595                 3600

Tyr Ala  Phe Cys Glu Ala Thr  Gly Val Pro Tyr Lys  Ser Phe Asp
    3605                 3610                 3615

Arg Val  Ala Lys Ile His Val  Cys Gly Asp Asp Gly  Phe Leu Ile
    3620                 3625                 3630

Thr Glu  Arg Ala Leu Gly Glu  Lys Phe Ala Ser Lys  Gly Val Gln
    3635                 3640                 3645

Ile Leu  Tyr Glu Ala Gly Lys  Pro Gln Lys Ile Thr  Glu Gly Asp
    3650                 3655                 3660

Lys Met  Lys Val Ala Tyr Gln  Phe Asp Asp Ile Glu  Phe Cys Ser
    3665                 3670                 3675

His Thr  Pro Ile Gln Val Arg  Trp Ser Asp Asn Thr  Ser Ser Tyr
    3680                 3685                 3690

Met Pro  Gly Arg Asn Thr Thr  Thr Ile Leu Ala Lys  Met Ala Thr
    3695                 3700                 3705

Arg Leu  Asp Ser Ser Gly Glu  Arg Gly Thr Ile Ala  Tyr Glu Lys
    3710                 3715                 3720

Ala Val  Ala Phe Ser Phe Leu  Leu Met Tyr Ser Trp  Asn Pro Leu
    3725                 3730                 3735

Ile Arg  Arg Ile Cys Leu Leu  Val Leu Ser Thr Glu  Leu Gln Val
    3740                 3745                 3750

Lys Pro  Gly Lys Ser Thr Thr  Tyr Tyr Tyr Glu Gly  Asp Pro Ile
    3755                 3760                 3765

Ser Ala  Tyr Lys Glu Val Ile  Gly His Asn Leu Phe  Asp Leu Lys
    3770                 3775                 3780

Arg Thr  Ser Phe Glu Lys Leu  Ala Lys Leu Asn Leu  Ser Met Ser
    3785                 3790                 3795

Val Leu  Gly Ala Trp Thr Arg  His Thr Ser Lys Arg  Leu Leu Gln
    3800                 3805                 3810

Asp Cys  Val Asn Met Gly Val  Lys Glu Gly Asn Trp  Leu Val Asn
    3815                 3820                 3825

Ala Asp  Arg Leu Val Ser Ser  Lys Thr Gly Asn Arg  Tyr Val Pro
    3830                 3835                 3840

Gly Glu  Gly His Thr Leu Gln  Gly Arg His Tyr Glu  Glu Leu Val
```

-continued

```
    3845                3850                3855

Leu Ala  Arg Lys Gln Ile Asn  Ser Phe Gln Gly Thr  Asp Arg Tyr
    3860                3865                3870

Asn Leu  Gly Pro Ile Val Asn  Met Val Leu Arg Arg  Leu Arg Val
    3875                3880                3885

Met Met  Met Thr Leu Ile Gly  Arg Gly Val
    3890                3895


<210> SEQ ID NO 3
<211> LENGTH: 12285
<212> TYPE: DNA
<213> ORGANISM: Classical Swine Fever Virus

<400> SEQUENCE: 3

agttcattct cgtgtacatg attggacaaa tcaaaatctc aatttggttc agggcctccc     60

tccagcgacg gccgagctgg gctagccatg cccacagtag gactagcaaa cggagggact    120

agccgtagtg gcgagctccc tgggtggtct aagtcctgag tacaggacag tcgtcagtag    180

ttcgacgtga gcagaagccc acctcgagat gctatgtgga cgagggcatg cccaagacac    240

accttaaccc tagcgggggt cgttagggtg aaatcacacc atgtgatggg agtacgacct    300

gatagggtgc tgcagaggcc cactattagg ctagtataaa aatctctgct gtacatggca    360

catggagttg aatcattttg aacttttata caaaacaaac aaacaaaaac caatgggagt    420

ggaggaaccg gtatacgatg taacggggag accattgttt ggagacccaa gtgaggtaca    480

cccacaatca acattgaagc taccacatga tagggggaga ggcaacatca aaacaacact    540

gaagaaccta cctaggagag gtgactgcag gagtggcaac cacctaggcc cggttagtgg    600

gatatatgta aagcccggcc ctgtctttta tcaggactac atgggcccag tctatcatag    660

agcccctcta gagtttttg acgaagcaca gttttgtgag gtgaccaaaa ggataggtag    720

ggtgacaggt agtgacggaa agctttacca tatatacgtg tgcatcgatg gttgcatcct    780

gctgaagcta gccaagaggg gcgagccaag aaccctgaag tggattagaa atctcaccga    840

ctgtccattg tgggttacca gttgttctga tgatggtgca agtgcaagta aagagaagaa    900

accagatagg atcaacaagg gtaaattaaa gatagcccca aaagagcatg agaaggacag    960

caggactaag ccacctgatg ctacgattgt agtggaagga gtaaaatacc aggtcaaaaa   1020

gaaaggtaaa gttaagggaa agaataccca agacggcctg taccacaaca agaataaacc   1080

accagaatct aggaagaaat tagaaaaagc cctattggca tgggcagtga tagcaattat   1140

gttataccaa cctgttgcag ccgaaaatat aactcaatgg aacctgagtg acaacggtac   1200

caatggtatc cagcacgcta tgtaccttag aggagtcagc agaagcttgc atgggatctg   1260

gccagaaaaa atatgcaaag gagtccccac ctacctggcc acagacacgg aactgagaga   1320

aatacaggga atgatggatg ccagcgaggg gacaaactat acgtgctgta agttacagag   1380

acatgaatgg aacaaacatg gatggtgtaa ctggtataac atagacccct ggatacagtt   1440

gatgaataga acccaagcaa acttggcaga aggccctccg agcaaggagt gcgccgtgac   1500

ttgcaggtac gataaaaatg ctgacattaa cgtggtcacc caggccagaa acaggccaac   1560

caccctaact ggctgcaaga aagggaaaaa tttttctttt gcgggtacag ttatagaggg   1620

cccatgtaat ttcaacgttt ctgttgagga tatcttatat ggggatcatg agtgtggcag   1680

tctactccag gatacggctc tatacctagt agatggaatg accaacacta tagagagagc   1740

caggcaggga gccgcgaggg tgacatcttg gctagggagg caactcagaa ctgccgggaa   1800
```

-continued

```
gaggttggag ggcagaagca aaacctggtt tggtgcctat gccctatcac cttattgtaa   1860
tgtgacaagc aaaatagggt acatatggta cactaacaac tgtaccccgg cttgcctccc   1920
caaaaataca aagataatag gccccggtaa atttgacact aacgcggaag acggaaagat   1980
tctccatgag atgggggggcc acctatcaga atttctgctg ctctctctgg tcgttctgtc   2040
tgacttcgcc cctgaaacag ccagcgcgtt atacctcatt ttgcactacg tgatccctca   2100
atcccatgaa gaacctgaag gctgtgacac aaaccagctg aatttaacag tggaactcag   2160
gactgaagac gtgataccat catcagtctg gaatgttggc aaatatgtgt gtgttagacc   2220
agactggtgg ccatatgaaa ccaaggtggc tttgttattt gaagaggcag gacaggtcgt   2280
aaagttagcc ttgcgggcac tgagggattt aaccagggtc tggaatagcg catcaaccac   2340
ggcattcctc atctgcttga taaaagtatt aagaggacag gtcgtgcaag gtgtgatatg   2400
gctgttactg gtaactgggg cacaaggccg gctagcctgc aaggaagatc acaggtacgc   2460
tatatcaaca accaatgaga tagggctact tggggccgaa ggtctcacta ccacctggaa   2520
agaatacaac cacaatttgc aactggatga tgggaccgtc aaggccatct gcatggcagg   2580
ttcctttaaa gtcacagcac ttaatgtggt tagtaggagg tatctggcat cattacataa   2640
ggacgcttta cccacttccg tgacattcga gctcctgttc gacgggacca gcccattgac   2700
cgaggaaatg ggagatgact tcgggttcgg actgtgtccg tatgatacga gccctgtagt   2760
caagggaaag tacaacacaa ccttgttgaa tggtagtgca ttctacctag tttgcccaat   2820
agggtggacg ggtgttatag agtgcacggc agtgagcccg acaactctga gaacagaagt   2880
ggtaaagacc ttcagaagag agaaaccctt tccgtacaga agggattgtg tgaccactac   2940
agtggaaaat gaagatctat tctactgtaa atggggggggc aattggacat gtgtgaaagg   3000
tgaaccagtg acctacacgg gggggccagt aaaacaatgc agatggtgtg gcttcgactt   3060
caatgagcct gacggactcc cacactaccc catagtaag tgcattttgg caaatgagac   3120
aggttacaga atagtggatt caacggactg taacagagat ggcgttgtaa tcagcacaga   3180
ggggagtcat gagtgcttga ttggtaacac aactgtcaag gtgcatgcat tagatgaaag   3240
actaggccct atgccatgca ggcctaagga gatcgtctct agtgcgggac ctgtaaggaa   3300
aacttcctgt acattcaact acgcaaaaac tctgaggaac aggtattatg agcccaggga   3360
cagctatttc caacaatata tgctcaaggg cgagtatcag tactggtttg atctggatgt   3420
gaccgaccgc cactcagatt acttcgcaga attcattgtc ttggtggtgg tggcactgtt   3480
gggaggaaga tatgtcctgt ggctaatagt gacctacata gttctaacag aacaactcgc   3540
cgctggtcta cagttaggcc agggtgaggt agtgttaata gggaacttaa tcacccacac   3600
agatattgag gttgtagtat atttcttact gctctatttg gtcatgagag atgagcctat   3660
aaagaaatgg atactactgc tgttccatgc tatgaccaac aatccagtta agaccataac   3720
agtggcactg ctcatggtta gcggggttgc caagggtgga aagatagatg gtggttggca   3780
gcggctgccg gagaccaact ttgatatcca actcgcgctg acagttatag tagtcgctgt   3840
gatgttgctg gcaaagaaag atccgactac cgtccccttg gttataacgg tggcaaccct   3900
gagaacggct aagataacta atggacttag tacagatcta gccatagcta cagtgtcaac   3960
agctttgcta acctggacct acattagtga ctattataaa tacaagacct tgctacagta   4020
ccttattagc acagtgacag gtatcttctt gataagggta ctgaaggggg taggtgagtt   4080
agatttacac accccaacct taccatctta cagacccctc ttcttcatcc tcgtgtacct   4140
catttccact gcagtggtaa caagatggaa tctggacata gccggattgc tgctgcagtg   4200
```

-continued

```
tgtcccaacc cttttaatgg ttttcacgat gtgggcagac atccttaccc tgatcctcat   4260
actgcctact tacgagttga caaaactata ttacctcaag gaagtgaaga ttggggcaga   4320
aaggggctgg ttgtggaaga ccaacttcaa gagggtaaat gacatatacg aagttgacca   4380
agctggtgag gggtgtacc ttttcccatc aaaacaaaag acaggtacaa taacaggtac    4440
tatgttgcca ttgatcaaag ccatactcat aagttgcatc agcaataagt ggcaatttat   4500
atatctattg tacttgatat tcgaagtgtc ttactacctt cacaagaaga tcatagatga   4560
aatagcagga gggaccaact tcatctcgag acttgtagcc gctctgattg aagccaattg   4620
ggcctttgac aacgaagaag ttagaggttt aaagaagttc ttcctgctgt ctagtagggt   4680
taaagaactg atcatcaaac acaaagtgag gaatgaagtg atggtccact ggtttggcga   4740
cgaagaggtc tatgggatgc cgaagctggt tggcttagtc aaggcagcaa cactgagtaa   4800
aaataaacat tgtattttgt gcaccgtctg tgaaaacaga gagtggagag gagaaacctg   4860
cccaaaatgc ggccgttttg ggccaccagt gacctgtggc atgaccctag ccgactttga   4920
agaaaaacac tataagagga ttttctttag agaggatcaa tcagaagggc cggttaggga   4980
ggagtatgca gggtatctgc aatatagagc cagagggcaa ttattcctga ggaatctccc   5040
ggtgctagca acaaaagtca agatgctcct ggtcggaaat cttgggacgg aggtgggga    5100
tttggaacac cttggctggg tgctcagagg gcctgccgtt tgcaagaagg ttaccgaaca   5160
tgagaaatgc accacatcca taatggacaa attaactgct ttcttcggtg ttatgccaag   5220
gggcaccaca cctagagccc ctgtgagatt ccccacctct ctcttaaaga taagaagggg   5280
gctggaaact ggctgggcgt acacacacca aggtggcatc agttcagtgg accatgtcac   5340
ttgtgggaaa gacttactgg tatgtgacac tatgggccgg acaagggttg tttgccaatc   5400
aaataacaag atgacagacg agtccgagta tggagttaaa actgactccg gatgcccgga   5460
gggagctagg tgttacgtgt tcaacccaga ggcagttaac atatccggga ctaaaggagc   5520
catggtccac ttacaaaaaa ctggaggaga attcacctgt gtgacagcat cagggactcc   5580
ggccttcttt gatctcaaga acctcaaagg ctggtcaggg ctgccgatat ttgaggcatc   5640
aagtggaaga gtagtcggca gggttaaggt cgggaagaat gaggactcta aaccaaccaa   5700
gcttatgagt ggaatacaaa cagtctccaa aagtaccaca gacttgacag aaatggtaaa   5760
gaaaataaca accatgaaca ggggagaatt cagacaaata acccttgcca caggtgccgg   5820
aaaaaccacg gaactcccta gatcagtcat agaagagata ggaaggcata agagggtctt   5880
ggtcttgatc cctctgaggg cggcagcaga gtcagtatac caatatatga gacaaaaaca   5940
cccaagcata gcattcaact tgaggatagg ggagatgaag gaaggggaca tggccacagg   6000
gataacctat gcctcatatg gttacttctg tcagatgcca caacctaagc tgcgagccgc   6060
gatggttgag tactccttca tattccttga tgagtaccac tgtgccaccc ccgaacaatt   6120
ggctatcatg ggaaagatcc acagattttc agagaacctg cgggtagtag ccatgaccgc   6180
aacaccagca ggcacggtaa caactacagg gcaaaaacac cctatagaag aatacatagc   6240
cccagaagtg atgaaggggg aagacttagg ttcagagtac ttggacatag ctggactaaa   6300
gataccagta gaggagatga agagtaacat gctggtcttt gtgcccacaa ggaacatggc   6360
tgtagagacg gcaaagaaac tgaaagctaa gggttataac tcaggctact attatagtgg   6420
agaggatcca tctaacctga gggtggtaac atcacagtcc ccgtacgtgg tggtagcaac   6480
caacgcaata gaatcaggtg ttactctccc agacttggat gtggtcgtcg acacagggct   6540
```

```
taagtgtgaa aagaggatac ggctgtcacc taagatgccc ttcatagtga cgggcctgaa   6600
gagaatggct gtcacgattg gggaacaagc ccagagaagg gggagagttg ggagagtgaa   6660
gcctgggaga tactacagga gtcaagaaac ccccgttggt tccaaagatt accattacga   6720
cctactgcaa gcacagaggt acggtataga agatgggata aacatcacca aatcttttag   6780
agagatgaat tatgattgga gcctttatga ggaggatagt ctgatgatta cacaattgga   6840
aatcctcaac aatctgttga tatcagaaga gctaccaatg gcagtaaaaa atataatggc   6900
caggactgac cacccagaac caatccaact ggcgtacaac agctacgaaa cgcaggtgcc   6960
agtgctattc ccaaaaataa aaaatggaga ggtgactgac agttacgata actatacctt   7020
cctcaacgca agaaagctgg gggatgatgt acctccctac gtgtatgcca cagaggatga   7080
ggacttagcg gtagagctgc tgggcttaga ctggccggac cctgggaacc aaggaaccgt   7140
ggaggctggt agagcactaa aacaagtagt tggtctatca acagctgaga acgccctgtt   7200
agtagcttta ttcggctatg taggatatca ggcactctca aagaggcata taccagtagt   7260
cacagacata tattcaattg aagatcacag gttggaagac accacacacc tacagtatgc   7320
cccgaatgct atcaagacgg aggggaagga gacagaattg aaggagctag ctcaggggga   7380
tgtgcagaga tgtatggaag ctatgactaa ttatgcaaga gatggcatcc aattcatgaa   7440
gtctcaggca ctgaaagtga aagaaacccc cacttacaaa gagacaatgg acaccgtggc   7500
ggactatgta aagaagttca tggaggcact ggcggacagc aaagaagaca tcataaaata   7560
tgggttgtgg gggacgcaca caaccttata taagagcatc ggtgctaggc ttgggaacga   7620
gactgcgttc gctaccctgg tcgtgaaatg gctggcattt gggggagaat caatagcaga   7680
ccatgtcaaa caagcggcca cagacttggt cgtttactat atcatcaaca gacctcagtt   7740
cccaggagac acggagacac aacaggaagg aaggaaattt gtagccagcc tactggtctc   7800
agccctggct acttacactt acaaaagctg gaattacaat aatctgtcca agatagttga   7860
accggctttg gctactctgc cctatgccgc cacagctctc aagctattcg cccccactcg   7920
attggagagc gttgtcatac tgagtaccgc aatctacaaa acctacctat caatcaggcg   7980
cggaaaaagc gatggtttgc taggcacagg ggttagtgcg gctatggaaa tcatgtcaca   8040
aaacccagta tctgtgggta tagcggtcat gctaggggtg ggggccgtag cggcccacaa   8100
tgcaatcgaa gccagtgagc agaagagaac actactcatg aaagtttttg taaagaactt   8160
cttggatcag gcagccactg atgaattagt caaggagagc cctgagaaaa taataatggc   8220
tttgtttgaa gcagtgcaga cagtcggcaa ccctcttaga ctggtatacc acctttacgg   8280
agtttttttac aaagggtggg aggcaaaaga gttggcccaa aggacagccg gtaggaatct   8340
tttcactttg ataatgtttg aggctgtgga actactggga gtagatagcg aaggaaagat   8400
ccgccagcta tcaagcaatt acatactaga gctcctgtat aagttccgtg acagtatcaa   8460
gtccagcgtg aggcagatgg caatcagctg ggcccctgcc ccttttagtt gtgattggac   8520
accgacggat gacagaatag ggcttcccca agataatttc ctccgagtgg agacaaaatg   8580
cccctgtggt tacaagatga aagcagttaa gaattgtgct ggggagttga gactcttaga   8640
agaggaaggc tcatttctct gcaggaataa attcgggaga ggttcacgga actacagggt   8700
gacaaaatac tatgatgaca atctatcaga aataaagcca gtgataagaa tggaaggaca   8760
tgtggaactc tactacaagg gagccactat taaactggat ttcaacaaca gtaaaacaat   8820
attggcaacc gataaatggg aggtcgatca ctccactctg gtcagggtgc tcaagaggca   8880
cacaggggct ggatatcgtg ggcatacct gggtgagaaa ccgaaccaca aacatctgat   8940
```

```
agagagggac tgcgcaacca tcaccaaaga taaggtttgt tttctcaaga tgaagagagg   9000
gtgtgcattt acttatgact tatcccttca caaccttacc cggctgatcg aattggtaca   9060
caagaataac ttggaagaca aagagattcc tgccgttacg gtcacaacct ggctggctta   9120
cacatttgta aatgaagata tagggaccat aaaaccagcc ttcggggaga aaataacacc   9180
agagatgcag gaggagataa ccttgcagcc tgctgtagtg gtggatgcaa ctgacgtgac   9240
cgtgaccgtg gtaggggaaa cccctactat gactacaggg gagaccccaa caacgttcac   9300
cagctcaggt ccagacccga aaggccaaca agttttaaaa ctgggagtag gtgaaggcca   9360
ataccccggg actaatccac agagagcaag cctgcacgaa gccatacaaa gcgcagatga   9420
aaggccctct gtgttgatat tggggtctga taaagccacc tctaatagag tgaaaactgt   9480
aaagaatgtg aaggtataca gaggcaggga cccactagaa gtgagagata tgatgaggag   9540
gggaaagatc ctagtcatag ccctgtctag ggttgataat gctctattga aatttgtaga   9600
ttacaaaggc acctttctaa ctagagagac cctggaggca ttaagtttgg gtaggccaaa   9660
aaagaaaaac ataaccaagg cagaagcaca gtggttgctg cgcctcgaag accaaatgga   9720
agagctaccc gattggttcg cagccgggga acccattttt ttagaggcca atattaaaca   9780
tgacaggtat catctggtag gggatatagc tactatcaaa gagaaagcca aacaattggg   9840
ggctacagac tctacaaaga tatccaagga ggttggtgca aaagtatatt ctatgaaatt   9900
gagtaattgg gtgatgcaag aagaaaacaa acagagcaac ttgacccccct tatttgaaga   9960
gctcctacag cagtgtccac ccggaggcca aaacaaaact gcacatatgg tctctgctta  10020
ccaactagct caagggaact ggatgccaac cagctgccat gtttttatgg ggaccatatc  10080
tgccagaagg actaagaccc atccatatga agcatatgtc aagttaaggg agttggtaga  10140
ggaacacaag atgaaaacat tgtgtcccgg atcaagtctg cgtaagcaca atgaatgggt  10200
aattggcaag atcaaatacc agggcaacct gaggaccaaa cacatgttga accccggcaa  10260
ggtggcagag caactgcaca gagaaggaca cagacacaat gtgtataaca agacaatagg  10320
ctcagtgatg acagctactg gcatcaggtt ggagaagttg cccgtggtta gggcccagac  10380
agacacaacc aacttccacc aagcaataag ggataagata gacaaggaag agaatctaca  10440
gaccccgggt ttacataaga aactaatgga agttttcaat gcattgaaac gacccgagtt  10500
agagtcctcc tatgacgctg tggaatggga ggaattggag agaggaataa acagaaaggg  10560
tgctgctggt ttctttgaac gcaaaaacat aggggagata ttggattcag agaaaaataa  10620
agtagaagag attattgaca atctgaaaaa gggtagaaat atcaaatact atgaaaccgc  10680
aatcccaaaa aatgaaaaga gggatgtcaa tgatgactgg accgcaggtg actttgtgga  10740
cgagaagaaa cccagagtca tacaataccc tgaagcaaaa acaaggctgg ccatcaccaa  10800
ggtgatgtat aagtgggtga agcagaagcc agtagtcata cccgggtatg aagggaagac  10860
acctctgttc caaatttttg acaaagtaaa gaaggaatgg gatcaattcc aaaatccagt  10920
ggcagtgagc ttcgacacta aggcgtggga cacccaggtg accacaaatg atctggagct  10980
gataaaggac atacaaaagt actacttcaa gaagaaatgg cataaattta ttgacaccct  11040
gactatgcat atgtcagaag tacccgtaat cactgctgat ggggaggtgt atataaggaa  11100
agggcaaaga ggtagtggac agcccgacac aagcgcaggc aacagcatgc taaatgtgtt  11160
aacaatggtt tatgccttct gcgaggccac aggggtaccc tacaagagtt ttgacagggt  11220
ggcaaaaatt catgtgtgcg gggacgatgg tttcctgatc acagagagag ctctcggcga  11280
```

```
gaaattcgca agcaagggag tccaaatcct gtatgaagct gggaagcccc agaagatcac  11340

tgaaggggac aaaatgaaag tggcctacca atttgatgat attgagtttt gctcccatac  11400

accaatacaa gtaaggtggt cagataacac ttctagctac atgccaggga gaaatacaac  11460

cacaatcctg gctaaaatgg ccacaaggtt agattccagt ggtgagaggg gtaccatagc  11520

gtacgagaaa gcagtagcat tcagcttcct gctaatgtat tcctggaacc cactaatcag  11580

aaggatttgc ttattggtac tatcaactga actgcaagtg aaaccaggga agtcaaccac  11640

ttactattat gaaggggacc cgatatctgc ctacaaggaa gtcatcggcc acaatctttt  11700

cgatctcaag agaacaagct tcgagaagct ggccaagtta aatctcagca tgtccgtact  11760

cggggcctgg actagacaca ccagcaaaag actactacaa gactgtgtca atatgggtgt  11820

taaagagggc aactggttag tcaatgcaga cagactggtg agtagtaaga ctggaaatag  11880

gtatgtacct ggagaaggcc acaccctgca agggagacat tatgaagaac tggtgttggc  11940

aagaaaacag atcaacagct tccaagggac agacaggtac aatctaggcc caatagtcaa  12000

catggtgtta aggaggctga gagtcatgat gatgaccctg atagggagag ggtatgagt  12060

gcgggtgacc cgcgatctgg acccgtcagt aggaccctat tgtagataac actaattttt  12120

tatttattta gatattacta tttatttatt tatttattta ttgaatgagt aagaactggt  12180

acaaactacc tcatgttacc acactacact cattttaaca gcactttagc tggaaggaaa  12240

attcctgacg tccacagttg gactaaggta atttcctaac ggccc                 12285
```

<210> SEQ ID NO 4
<211> LENGTH: 3898
<212> TYPE: PRT
<213> ORGANISM: Classical Swine Fever Virus

<400> SEQUENCE: 4

```
Met Glu Leu Asn His Phe Glu Leu Leu Tyr Lys Thr Asn Lys Gln Lys
1               5                   10                  15

Pro Met Gly Val Glu Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Leu Thr Asp
145                 150                 155                 160

Cys Pro Leu Trp Val Thr Ser Cys Ser Asp Asp Gly Ala Ser Ala Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Lys Pro Pro Asp Ala Thr
```

-continued

```
        195                 200                 205

Ile Val Val Glu Gly Val Lys Tyr Gln Val Lys Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
                245                 250                 255

Ile Ala Ile Met Leu Tyr Gln Pro Val Ala Ala Glu Asn Ile Thr Gln
            260                 265                 270

Trp Asn Leu Ser Asp Asn Gly Thr Asn Gly Ile Gln His Ala Met Tyr
        275                 280                 285

Leu Arg Gly Val Ser Arg Ser Leu His Gly Ile Trp Pro Glu Lys Ile
    290                 295                 300

Cys Lys Gly Val Pro Thr Tyr Leu Ala Thr Asp Thr Glu Leu Arg Glu
305                 310                 315                 320

Ile Gln Gly Met Met Asp Ala Ser Glu Gly Thr Asn Tyr Thr Cys Cys
                325                 330                 335

Lys Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Ala Asn Leu
        355                 360                 365

Ala Glu Gly Pro Pro Ser Lys Glu Cys Ala Val Thr Cys Arg Tyr Asp
    370                 375                 380

Lys Asn Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
            420                 425                 430

Tyr Gly Asp His Glu Cys Gly Ser Leu Leu Gln Asp Thr Ala Leu Tyr
        435                 440                 445

Leu Val Asp Gly Met Thr Asn Thr Ile Glu Arg Ala Arg Gln Gly Ala
    450                 455                 460

Ala Arg Val Thr Ser Trp Leu Gly Arg Gln Leu Arg Thr Ala Gly Lys
465                 470                 475                 480

Arg Leu Glu Gly Arg Ser Lys Thr Trp Phe Gly Ala Tyr Ala Leu Ser
                485                 490                 495

Pro Tyr Cys Asn Val Thr Ser Lys Ile Gly Tyr Ile Trp Tyr Thr Asn
            500                 505                 510

Asn Cys Thr Pro Ala Cys Leu Pro Lys Asn Thr Lys Ile Ile Gly Pro
        515                 520                 525

Gly Lys Phe Asp Thr Asn Ala Glu Asp Gly Lys Ile Leu His Glu Met
    530                 535                 540

Gly Gly His Leu Ser Glu Phe Leu Leu Leu Ser Leu Val Val Leu Ser
545                 550                 555                 560

Asp Phe Ala Pro Glu Thr Ala Ser Ala Leu Tyr Leu Ile Leu His Tyr
                565                 570                 575

Val Ile Pro Gln Ser His Glu Glu Pro Glu Gly Cys Asp Thr Asn Gln
            580                 585                 590

Leu Asn Leu Thr Val Glu Leu Arg Thr Glu Asp Val Ile Pro Ser Ser
        595                 600                 605

Val Trp Asn Val Gly Lys Tyr Val Cys Val Arg Pro Asp Trp Trp Pro
    610                 615                 620
```

-continued

```
Tyr Glu Thr Lys Val Ala Leu Leu Phe Glu Glu Ala Gly Gln Val Val
625                 630                 635                 640

Lys Leu Ala Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
            660                 665                 670

Gln Val Val Gln Gly Val Ile Trp Leu Leu Leu Val Thr Gly Ala Gln
        675                 680                 685

Gly Arg Leu Ala Cys Lys Glu Asp His Arg Tyr Ala Ile Ser Thr Thr
    690                 695                 700

Asn Glu Ile Gly Leu Leu Gly Ala Glu Gly Leu Thr Thr Thr Trp Lys
705                 710                 715                 720

Glu Tyr Asn His Asn Leu Gln Leu Asp Asp Gly Thr Val Lys Ala Ile
                725                 730                 735

Cys Met Ala Gly Ser Phe Lys Val Thr Ala Leu Asn Val Val Ser Arg
            740                 745                 750

Arg Tyr Leu Ala Ser Leu His Lys Asp Ala Leu Pro Thr Ser Val Thr
        755                 760                 765

Phe Glu Leu Leu Phe Asp Gly Thr Ser Pro Leu Thr Glu Glu Met Gly
    770                 775                 780

Asp Asp Phe Gly Phe Gly Leu Cys Pro Tyr Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Glu Lys
        835                 840                 845

Pro Phe Pro Tyr Arg Arg Asp Cys Val Thr Thr Thr Val Glu Asn Glu
    850                 855                 860

Asp Leu Phe Tyr Cys Lys Trp Gly Gly Asn Trp Thr Cys Val Lys Gly
865                 870                 875                 880

Glu Pro Val Thr Tyr Thr Gly Gly Pro Val Lys Gln Cys Arg Trp Cys
                885                 890                 895

Gly Phe Asp Phe Asn Glu Pro Asp Gly Leu Pro His Tyr Pro Ile Gly
            900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
    930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Ala Gly
                965                 970                 975

Pro Val Arg Lys Thr Ser Cys Thr Phe Asn Tyr Ala Lys Thr Leu Arg
            980                 985                 990

Asn Arg Tyr Tyr Glu Pro Arg Asp  Ser Tyr Phe Gln Gln  Tyr Met Leu
        995                 1000                1005

Lys Gly  Glu Tyr Gln Tyr Trp  Phe Asp Leu Asp Val  Thr Asp Arg
    1010                1015                1020

His Ser  Asp Tyr Phe Ala Glu  Phe Ile Val Leu Val  Val Val Ala
    1025                1030                1035
```

-continued

```
Leu Leu  Gly Gly Arg Tyr Val  Leu Trp Leu Ile Val  Thr Tyr Ile
    1040                 1045                 1050

Val Leu  Thr Glu Gln Leu Ala  Ala Gly Leu Gln Leu  Gly Gln Gly
    1055                 1060                 1065

Glu Val  Val Leu Ile Gly Asn  Leu Ile Thr His Thr  Asp Ile Glu
    1070                 1075                 1080

Val Val  Val Tyr Phe Leu Leu  Leu Tyr Leu Val Met  Arg Asp Glu
    1085                 1090                 1095

Pro Ile  Lys Lys Trp Ile Leu  Leu Leu Phe His Ala  Met Thr Asn
    1100                 1105                 1110

Asn Pro  Val Lys Thr Ile Thr  Val Ala Leu Leu Met  Val Ser Gly
    1115                 1120                 1125

Val Ala  Lys Gly Gly Lys Ile  Asp Gly Gly Trp Gln  Arg Leu Pro
    1130                 1135                 1140

Glu Thr  Asn Phe Asp Ile Gln  Leu Ala Leu Thr Val  Ile Val Val
    1145                 1150                 1155

Ala Val  Met Leu Leu Ala Lys  Lys Asp Pro Thr Thr  Val Pro Leu
    1160                 1165                 1170

Val Ile  Thr Val Ala Thr Leu  Arg Thr Ala Lys Ile  Thr Asn Gly
    1175                 1180                 1185

Leu Ser  Thr Asp Leu Ala Ile  Ala Thr Val Ser Thr  Ala Leu Leu
    1190                 1195                 1200

Thr Trp  Thr Tyr Ile Ser Asp  Tyr Tyr Lys Tyr Lys  Thr Leu Leu
    1205                 1210                 1215

Gln Tyr  Leu Ile Ser Thr Val  Thr Gly Ile Phe Leu  Ile Arg Val
    1220                 1225                 1230

Leu Lys  Gly Val Gly Glu Leu  Asp Leu His Thr Pro  Thr Leu Pro
    1235                 1240                 1245

Ser Tyr  Arg Pro Leu Phe Phe  Ile Leu Val Tyr Leu  Ile Ser Thr
    1250                 1255                 1260

Ala Val  Val Thr Arg Trp Asn  Leu Asp Ile Ala Gly  Leu Leu Leu
    1265                 1270                 1275

Gln Cys  Val Pro Thr Leu Leu  Met Val Phe Thr Met  Trp Ala Asp
    1280                 1285                 1290

Ile Leu  Thr Leu Ile Leu Ile  Leu Pro Thr Tyr Glu  Leu Thr Lys
    1295                 1300                 1305

Leu Tyr  Tyr Leu Lys Glu Val  Lys Ile Gly Ala Glu  Arg Gly Trp
    1310                 1315                 1320

Leu Trp  Lys Thr Asn Phe Lys  Arg Val Asn Asp Ile  Tyr Glu Val
    1325                 1330                 1335

Asp Gln  Ala Gly Glu Gly Val  Tyr Leu Phe Pro Ser  Lys Gln Lys
    1340                 1345                 1350

Thr Gly  Thr Ile Thr Gly Thr  Met Leu Pro Leu Ile  Lys Ala Ile
    1355                 1360                 1365

Leu Ile  Ser Cys Ile Ser Asn  Lys Trp Gln Phe Ile  Tyr Leu Leu
    1370                 1375                 1380

Tyr Leu  Ile Phe Glu Val Ser  Tyr Tyr Leu His Lys  Lys Ile Ile
    1385                 1390                 1395

Asp Glu  Ile Ala Gly Gly Thr  Asn Phe Ile Ser Arg  Leu Val Ala
    1400                 1405                 1410

Ala Leu  Ile Glu Ala Asn Trp  Ala Phe Asp Asn Glu  Glu Val Arg
    1415                 1420                 1425

Gly Leu  Lys Lys Phe Phe Leu  Leu Ser Ser Arg Val  Lys Glu Leu
```

-continued

```
    1430                1435                1440

Ile Ile  Lys His Lys Val Arg  Asn Glu Val Met Val  His Trp Phe
    1445                1450                1455

Gly Asp  Glu Glu Val Tyr Gly  Met Pro Lys Leu Val  Gly Leu Val
    1460                1465                1470

Lys Ala  Ala Thr Leu Ser Lys  Asn Lys His Cys Ile  Leu Cys Thr
    1475                1480                1485

Val Cys  Glu Asn Arg Glu Trp  Arg Gly Glu Thr Cys  Pro Lys Cys
    1490                1495                1500

Gly Arg  Phe Gly Pro Pro Val  Thr Cys Gly Met Thr  Leu Ala Asp
    1505                1510                1515

Phe Glu  Glu Lys His Tyr Lys  Arg Ile Phe Phe Arg  Glu Asp Gln
    1520                1525                1530

Ser Glu  Gly Pro Val Arg Glu  Glu Tyr Ala Gly Tyr  Leu Gln Tyr
    1535                1540                1545

Arg Ala  Arg Gly Gln Leu Phe  Leu Arg Asn Leu Pro  Val Leu Ala
    1550                1555                1560

Thr Lys  Val Lys Met Leu Leu  Val Gly Asn Leu Gly  Thr Glu Val
    1565                1570                1575

Gly Asp  Leu Glu His Leu Gly  Trp Val Leu Arg Gly  Pro Ala Val
    1580                1585                1590

Cys Lys  Lys Val Thr Glu His  Glu Lys Cys Thr Thr  Ser Ile Met
    1595                1600                1605

Asp Lys  Leu Thr Ala Phe Phe  Gly Val Met Pro Arg  Gly Thr Thr
    1610                1615                1620

Pro Arg  Ala Pro Val Arg Phe  Pro Thr Ser Leu Leu  Lys Ile Arg
    1625                1630                1635

Arg Gly  Leu Glu Thr Gly Trp  Ala Tyr Thr His Gln  Gly Gly Ile
    1640                1645                1650

Ser Ser  Val Asp His Val Thr  Cys Gly Lys Asp Leu  Leu Val Cys
    1655                1660                1665

Asp Thr  Met Gly Arg Thr Arg  Val Val Cys Gln Ser  Asn Asn Lys
    1670                1675                1680

Met Thr  Asp Glu Ser Glu Tyr  Gly Val Lys Thr Asp  Ser Gly Cys
    1685                1690                1695

Pro Glu  Gly Ala Arg Cys Tyr  Val Phe Asn Pro Glu  Ala Val Asn
    1700                1705                1710

Ile Ser  Gly Thr Lys Gly Ala  Met Val His Leu Gln  Lys Thr Gly
    1715                1720                1725

Gly Glu  Phe Thr Cys Val Thr  Ala Ser Gly Thr Pro  Ala Phe Phe
    1730                1735                1740

Asp Leu  Lys Asn Leu Lys Gly  Trp Ser Gly Leu Pro  Ile Phe Glu
    1745                1750                1755

Ala Ser  Ser Gly Arg Val Val  Gly Arg Val Lys Val  Gly Lys Asn
    1760                1765                1770

Glu Asp  Ser Lys Pro Thr Lys  Leu Met Ser Gly Ile  Gln Thr Val
    1775                1780                1785

Ser Lys  Ser Thr Thr Asp Leu  Thr Glu Met Val Lys  Lys Ile Thr
    1790                1795                1800

Thr Met  Asn Arg Gly Glu Phe  Arg Gln Ile Thr Leu  Ala Thr Gly
    1805                1810                1815

Ala Gly  Lys Thr Thr Glu Leu  Pro Arg Ser Val Ile  Glu Glu Ile
    1820                1825                1830
```

```
Gly Arg His Lys Arg Val Leu Val Leu Ile Pro Leu Arg Ala Ala
    1835                1840                1845

Ala Glu Ser Val Tyr Gln Tyr Met Arg Gln Lys His Pro Ser Ile
    1850                1855                1860

Ala Phe Asn Leu Arg Ile Gly Glu Met Lys Glu Gly Asp Met Ala
    1865                1870                1875

Thr Gly Ile Thr Tyr Ala Ser Tyr Gly Tyr Phe Cys Gln Met Pro
    1880                1885                1890

Gln Pro Lys Leu Arg Ala Ala Met Val Glu Tyr Ser Phe Ile Phe
    1895                1900                1905

Leu Asp Glu Tyr His Cys Ala Thr Pro Glu Gln Leu Ala Ile Met
    1910                1915                1920

Gly Lys Ile His Arg Phe Ser Glu Asn Leu Arg Val Val Ala Met
    1925                1930                1935

Thr Ala Thr Pro Ala Gly Thr Val Thr Thr Thr Gly Gln Lys His
    1940                1945                1950

Pro Ile Glu Glu Tyr Ile Ala Pro Glu Val Met Lys Gly Glu Asp
    1955                1960                1965

Leu Gly Ser Glu Tyr Leu Asp Ile Ala Gly Leu Lys Ile Pro Val
    1970                1975                1980

Glu Glu Met Lys Ser Asn Met Leu Val Phe Val Pro Thr Arg Asn
    1985                1990                1995

Met Ala Val Glu Thr Ala Lys Lys Leu Lys Ala Lys Gly Tyr Asn
    2000                2005                2010

Ser Gly Tyr Tyr Tyr Ser Gly Glu Asp Pro Ser Asn Leu Arg Val
    2015                2020                2025

Val Thr Ser Gln Ser Pro Tyr Val Val Val Ala Thr Asn Ala Ile
    2030                2035                2040

Glu Ser Gly Val Thr Leu Pro Asp Leu Asp Val Val Val Asp Thr
    2045                2050                2055

Gly Leu Lys Cys Glu Lys Arg Ile Arg Leu Ser Pro Lys Met Pro
    2060                2065                2070

Phe Ile Val Thr Gly Leu Lys Arg Met Ala Val Thr Ile Gly Glu
    2075                2080                2085

Gln Ala Gln Arg Arg Gly Arg Val Gly Arg Val Lys Pro Gly Arg
    2090                2095                2100

Tyr Tyr Arg Ser Gln Glu Thr Pro Val Gly Ser Lys Asp Tyr His
    2105                2110                2115

Tyr Asp Leu Leu Gln Ala Gln Arg Tyr Gly Ile Glu Asp Gly Ile
    2120                2125                2130

Asn Ile Thr Lys Ser Phe Arg Glu Met Asn Tyr Asp Trp Ser Leu
    2135                2140                2145

Tyr Glu Glu Asp Ser Leu Met Ile Thr Gln Leu Glu Ile Leu Asn
    2150                2155                2160

Asn Leu Leu Ile Ser Glu Glu Leu Pro Met Ala Val Lys Asn Ile
    2165                2170                2175

Met Ala Arg Thr Asp His Pro Glu Pro Ile Gln Leu Ala Tyr Asn
    2180                2185                2190

Ser Tyr Glu Thr Gln Val Pro Val Leu Phe Pro Lys Ile Lys Asn
    2195                2200                2205

Gly Glu Val Thr Asp Ser Tyr Asp Asn Tyr Thr Phe Leu Asn Ala
    2210                2215                2220
```

-continued

```
Arg Lys  Leu Gly Asp Asp Val  Pro Pro Tyr Val Tyr  Ala Thr Glu
    2225                 2230                 2235

Asp Glu  Asp Leu Ala Val Glu  Leu Leu Gly Leu Asp  Trp Pro Asp
    2240                 2245                 2250

Pro Gly  Asn Gln Gly Thr Val  Glu Ala Gly Arg Ala  Leu Lys Gln
    2255                 2260                 2265

Val Val  Gly Leu Ser Thr Ala  Glu Asn Ala Leu Leu  Val Ala Leu
    2270                 2275                 2280

Phe Gly  Tyr Val Gly Tyr Gln  Ala Leu Ser Lys Arg  His Ile Pro
    2285                 2290                 2295

Val Val  Thr Asp Ile Tyr Ser  Ile Glu Asp His Arg  Leu Glu Asp
    2300                 2305                 2310

Thr Thr  His Leu Gln Tyr Ala  Pro Asn Ala Ile Lys  Thr Glu Gly
    2315                 2320                 2325

Lys Glu  Thr Glu Leu Lys Glu  Leu Ala Gln Gly Asp  Val Gln Arg
    2330                 2335                 2340

Cys Met  Glu Ala Met Thr Asn  Tyr Ala Arg Asp Gly  Ile Gln Phe
    2345                 2350                 2355

Met Lys  Ser Gln Ala Leu Lys  Val Lys Glu Thr Pro  Thr Tyr Lys
    2360                 2365                 2370

Glu Thr  Met Asp Thr Val Ala  Asp Tyr Val Lys Lys  Phe Met Glu
    2375                 2380                 2385

Ala Leu  Ala Asp Ser Lys Glu  Asp Ile Ile Lys Tyr  Gly Leu Trp
    2390                 2395                 2400

Gly Thr  His Thr Thr Leu Tyr  Lys Ser Ile Gly Ala  Arg Leu Gly
    2405                 2410                 2415

Asn Glu  Thr Ala Phe Ala Thr  Leu Val Val Lys Trp  Leu Ala Phe
    2420                 2425                 2430

Gly Gly  Glu Ser Ile Ala Asp  His Val Lys Gln Ala  Ala Thr Asp
    2435                 2440                 2445

Leu Val  Val Tyr Tyr Ile Ile  Asn Arg Pro Gln Phe  Pro Gly Asp
    2450                 2455                 2460

Thr Glu  Thr Gln Gln Glu Gly  Arg Lys Phe Val Ala  Ser Leu Leu
    2465                 2470                 2475

Val Ser  Ala Leu Ala Thr Tyr  Thr Tyr Lys Ser Trp  Asn Tyr Asn
    2480                 2485                 2490

Asn Leu  Ser Lys Ile Val Glu  Pro Ala Leu Ala Thr  Leu Pro Tyr
    2495                 2500                 2505

Ala Ala  Thr Ala Leu Lys Leu  Phe Ala Pro Thr Arg  Leu Glu Ser
    2510                 2515                 2520

Val Val  Ile Leu Ser Thr Ala  Ile Tyr Lys Thr Tyr  Leu Ser Ile
    2525                 2530                 2535

Arg Arg  Gly Lys Ser Asp Gly  Leu Leu Gly Thr Gly  Val Ser Ala
    2540                 2545                 2550

Ala Met  Glu Ile Met Ser Gln  Asn Pro Val Ser Val  Gly Ile Ala
    2555                 2560                 2565

Val Met  Leu Gly Val Gly Ala  Val Ala Ala His Asn  Ala Ile Glu
    2570                 2575                 2580

Ala Ser  Glu Gln Lys Arg Thr  Leu Leu Met Lys Val  Phe Val Lys
    2585                 2590                 2595

Asn Phe  Leu Asp Gln Ala Ala  Thr Asp Glu Leu Val  Lys Glu Ser
    2600                 2605                 2610

Pro Glu  Lys Ile Ile Met Ala  Leu Phe Glu Ala Val  Gln Thr Val
```

```
    2615                2620                2625

Gly Asn Pro Leu Arg Leu Val Tyr His Leu Tyr Gly Val Phe Tyr
    2630                2635                2640

Lys Gly Trp Glu Ala Lys Glu Leu Ala Gln Arg Thr Ala Gly Arg
    2645                2650                2655

Asn Leu Phe Thr Leu Ile Met Phe Glu Ala Val Glu Leu Leu Gly
    2660                2665                2670

Val Asp Ser Glu Gly Lys Ile Arg Gln Leu Ser Ser Asn Tyr Ile
    2675                2680                2685

Leu Glu Leu Leu Tyr Lys Phe Arg Asp Ser Ile Lys Ser Ser Val
    2690                2695                2700

Arg Gln Met Ala Ile Ser Trp Ala Pro Ala Pro Phe Ser Cys Asp
    2705                2710                2715

Trp Thr Pro Thr Asp Asp Arg Ile Gly Leu Pro Gln Asp Asn Phe
    2720                2725                2730

Leu Arg Val Glu Thr Lys Cys Pro Cys Gly Tyr Lys Met Lys Ala
    2735                2740                2745

Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
    2765                2770                2775

Arg Val Thr Lys Tyr Tyr Asp Asp Asn Leu Ser Glu Ile Lys Pro
    2780                2785                2790

Val Ile Arg Met Glu Gly His Val Glu Leu Tyr Tyr Lys Gly Ala
    2795                2800                2805

Thr Ile Lys Leu Asp Phe Asn Asn Ser Lys Thr Ile Leu Ala Thr
    2810                2815                2820

Asp Lys Trp Glu Val Asp His Ser Thr Leu Val Arg Val Leu Lys
    2825                2830                2835

Arg His Thr Gly Ala Gly Tyr Arg Gly Ala Tyr Leu Gly Glu Lys
    2840                2845                2850

Pro Asn His Lys His Leu Ile Glu Arg Asp Cys Ala Thr Ile Thr
    2855                2860                2865

Lys Asp Lys Val Cys Phe Leu Lys Met Lys Arg Gly Cys Ala Phe
    2870                2875                2880

Thr Tyr Asp Leu Ser Leu His Asn Leu Thr Arg Leu Ile Glu Leu
    2885                2890                2895

Val His Lys Asn Asn Leu Glu Asp Lys Glu Ile Pro Ala Val Thr
    2900                2905                2910

Val Thr Thr Trp Leu Ala Tyr Thr Phe Val Asn Glu Asp Ile Gly
    2915                2920                2925

Thr Ile Lys Pro Ala Phe Gly Glu Lys Ile Thr Pro Glu Met Gln
    2930                2935                2940

Glu Glu Ile Thr Leu Gln Pro Ala Val Val Val Asp Ala Thr Asp
    2945                2950                2955

Val Thr Val Thr Val Val Gly Glu Thr Pro Thr Met Thr Thr Gly
    2960                2965                2970

Glu Thr Pro Thr Thr Phe Thr Ser Ser Gly Pro Asp Pro Lys Gly
    2975                2980                2985

Gln Gln Val Leu Lys Leu Gly Val Gly Glu Gly Gln Tyr Pro Gly
    2990                2995                3000

Thr Asn Pro Gln Arg Ala Ser Leu His Glu Ala Ile Gln Ser Ala
    3005                3010                3015
```

```
Asp Glu  Arg Pro Ser Val Leu  Ile Leu Gly Ser Asp  Lys Ala Thr
    3020                 3025                 3030

Ser Asn  Arg Val Lys Thr Val  Lys Asn Val Lys Val  Tyr Arg Gly
    3035                 3040                 3045

Arg Asp  Pro Leu Glu Val Arg  Asp Met Met Arg Arg  Gly Lys Ile
    3050                 3055                 3060

Leu Val  Ile Ala Leu Ser Arg  Val Asp Asn Ala Leu  Leu Lys Phe
    3065                 3070                 3075

Val Asp  Tyr Lys Gly Thr Phe  Leu Thr Arg Glu Thr  Leu Glu Ala
    3080                 3085                 3090

Leu Ser  Leu Gly Arg Pro Lys  Lys Lys Asn Ile Thr  Lys Ala Glu
    3095                 3100                 3105

Ala Gln  Trp Leu Leu Arg Leu  Glu Asp Gln Met Glu  Glu Leu Pro
    3110                 3115                 3120

Asp Trp  Phe Ala Ala Gly Glu  Pro Ile Phe Leu Glu  Ala Asn Ile
    3125                 3130                 3135

Lys His  Asp Arg Tyr His Leu  Val Gly Asp Ile Ala  Thr Ile Lys
    3140                 3145                 3150

Glu Lys  Ala Lys Gln Leu Gly  Ala Thr Asp Ser Thr  Lys Ile Ser
    3155                 3160                 3165

Lys Glu  Val Gly Ala Lys Val  Tyr Ser Met Lys Leu  Ser Asn Trp
    3170                 3175                 3180

Val Met  Gln Glu Glu Asn Lys  Gln Ser Asn Leu Thr  Pro Leu Phe
    3185                 3190                 3195

Glu Glu  Leu Leu Gln Gln Cys  Pro Pro Gly Gly Gln  Asn Lys Thr
    3200                 3205                 3210

Ala His  Met Val Ser Ala Tyr  Gln Leu Ala Gln Gly  Asn Trp Met
    3215                 3220                 3225

Pro Thr  Ser Cys His Val Phe  Met Gly Thr Ile Ser  Ala Arg Arg
    3230                 3235                 3240

Thr Lys  Thr His Pro Tyr Glu  Ala Tyr Val Lys Leu  Arg Glu Leu
    3245                 3250                 3255

Val Glu  Glu His Lys Met Lys  Thr Leu Cys Pro Gly  Ser Ser Leu
    3260                 3265                 3270

Arg Lys  His Asn Glu Trp Val  Ile Gly Lys Ile Lys  Tyr Gln Gly
    3275                 3280                 3285

Asn Leu  Arg Thr Lys His Met  Leu Asn Pro Gly Lys  Val Ala Glu
    3290                 3295                 3300

Gln Leu  His Arg Glu Gly His  Arg His Asn Val Tyr  Asn Lys Thr
    3305                 3310                 3315

Ile Gly  Ser Val Met Thr Ala  Thr Gly Ile Arg Leu  Glu Lys Leu
    3320                 3325                 3330

Pro Val  Val Arg Ala Gln Thr  Asp Thr Thr Asn Phe  His Gln Ala
    3335                 3340                 3345

Ile Arg  Asp Lys Ile Asp Lys  Glu Glu Asn Leu Gln  Thr Pro Gly
    3350                 3355                 3360

Leu His  Lys Lys Leu Met Glu  Val Phe Asn Ala Leu  Lys Arg Pro
    3365                 3370                 3375

Glu Leu  Glu Ser Ser Tyr Asp  Ala Val Glu Trp Glu  Glu Leu Glu
    3380                 3385                 3390

Arg Gly  Ile Asn Arg Lys Gly  Ala Ala Gly Phe Phe  Glu Arg Lys
    3395                 3400                 3405
```

-continued

```
Asn Ile  Gly Glu Ile Leu Asp  Ser Glu Lys Asn Lys  Val Glu Glu
    3410                3415                3420

Ile Ile  Asp Asn Leu Lys Lys  Gly Arg Asn Ile Lys  Tyr Tyr Glu
    3425                3430                3435

Thr Ala  Ile Pro Lys Asn Glu  Lys Arg Asp Val Asn  Asp Asp Trp
    3440                3445                3450

Thr Ala  Gly Asp Phe Val Asp  Glu Lys Lys Pro Arg  Val Ile Gln
    3455                3460                3465

Tyr Pro  Glu Ala Lys Thr Arg  Leu Ala Ile Thr Lys  Val Met Tyr
    3470                3475                3480

Lys Trp  Val Lys Gln Lys Pro  Val Val Ile Pro Gly  Tyr Glu Gly
    3485                3490                3495

Lys Thr  Pro Leu Phe Gln Ile  Phe Asp Lys Val Lys  Lys Glu Trp
    3500                3505                3510

Asp Gln  Phe Gln Asn Pro Val  Ala Val Ser Phe Asp  Thr Lys Ala
    3515                3520                3525

Trp Asp  Thr Gln Val Thr Thr  Asn Asp Leu Glu Leu  Ile Lys Asp
    3530                3535                3540

Ile Gln  Lys Tyr Tyr Phe Lys  Lys Lys Trp His Lys  Phe Ile Asp
    3545                3550                3555

Thr Leu  Thr Met His Met Ser  Glu Val Pro Val Ile  Thr Ala Asp
    3560                3565                3570

Gly Glu  Val Tyr Ile Arg Lys  Gly Gln Arg Gly Ser  Gly Gln Pro
    3575                3580                3585

Asp Thr  Ser Ala Gly Asn Ser  Met Leu Asn Val Leu  Thr Met Val
    3590                3595                3600

Tyr Ala  Phe Cys Glu Ala Thr  Gly Val Pro Tyr Lys  Ser Phe Asp
    3605                3610                3615

Arg Val  Ala Lys Ile His Val  Cys Gly Asp Asp Gly  Phe Leu Ile
    3620                3625                3630

Thr Glu  Arg Ala Leu Gly Glu  Lys Phe Ala Ser Lys  Gly Val Gln
    3635                3640                3645

Ile Leu  Tyr Glu Ala Gly Lys  Pro Gln Lys Ile Thr  Glu Gly Asp
    3650                3655                3660

Lys Met  Lys Val Ala Tyr Gln  Phe Asp Asp Ile Glu  Phe Cys Ser
    3665                3670                3675

His Thr  Pro Ile Gln Val Arg  Trp Ser Asp Asn Thr  Ser Ser Tyr
    3680                3685                3690

Met Pro  Gly Arg Asn Thr Thr  Thr Ile Leu Ala Lys  Met Ala Thr
    3695                3700                3705

Arg Leu  Asp Ser Ser Gly Glu  Arg Gly Thr Ile Ala  Tyr Glu Lys
    3710                3715                3720

Ala Val  Ala Phe Ser Phe Leu  Leu Met Tyr Ser Trp  Asn Pro Leu
    3725                3730                3735

Ile Arg  Arg Ile Cys Leu Leu  Val Leu Ser Thr Glu  Leu Gln Val
    3740                3745                3750

Lys Pro  Gly Lys Ser Thr Thr  Tyr Tyr Tyr Glu Gly  Asp Pro Ile
    3755                3760                3765

Ser Ala  Tyr Lys Glu Val Ile  Gly His Asn Leu Phe  Asp Leu Lys
    3770                3775                3780

Arg Thr  Ser Phe Glu Lys Leu  Ala Lys Leu Asn Leu  Ser Met Ser
    3785                3790                3795

Val Leu  Gly Ala Trp Thr Arg  His Thr Ser Lys Arg  Leu Leu Gln
```

-continued

```
    3800                3805                3810

Asp Cys  Val Asn Met Gly Val  Lys Glu Gly Asn Trp  Leu Val Asn
    3815                3820                3825

Ala Asp  Arg Leu Val Ser Ser  Lys Thr Gly Asn Arg  Tyr Val Pro
    3830                3835                3840

Gly Glu  Gly His Thr Leu Gln  Gly Arg His Tyr Glu  Glu Leu Val
    3845                3850                3855

Leu Ala  Arg Lys Gln Ile Asn  Ser Phe Gln Gly Thr  Asp Arg Tyr
    3860                3865                3870

Asn Leu  Gly Pro Ile Val Asn  Met Val Leu Arg Arg  Leu Arg Val
    3875                3880                3885

Met Met  Met Thr Leu Ile Gly  Arg Gly Val
    3890                3895


<210> SEQ ID NO 5
<211> LENGTH: 10
<212> TYPE: PRT
<213> ORGANISM: Classical Swine Fever Virus

<400> SEQUENCE: 5

Cys Lys Trp Gly Gly Asn Trp Thr Cys Val
1               5                   10


<210> SEQ ID NO 6
<211> LENGTH: 61
<212> TYPE: DNA
<213> ORGANISM: Artificial Sequence
<220> FEATURE:
<223> OTHER INFORMATION: Chemically Synthesized

<400> SEQUENCE: 6

attctactgt aaatgggggg gcaatgatac atgtacgaaa ggtgaaccag tgacctacac     60

g                                                                     61


<210> SEQ ID NO 7
<211> LENGTH: 61
<212> TYPE: DNA
<213> ORGANISM: Artificial Sequence
<220> FEATURE:
<223> OTHER INFORMATION: Chemically Synthesized

<400> SEQUENCE: 7

cgtgtaggtc actggttcac ctttcgtaca tgtatcattg cccccccatt tacagtagaa     60

t                                                                     61


<210> SEQ ID NO 8
<211> LENGTH: 46
<212> TYPE: DNA
<213> ORGANISM: Artificial Sequence
<220> FEATURE:
<223> OTHER INFORMATION: Chemically Synthesized

<400> SEQUENCE: 8

tggaaaatga agatctattc tactgtaaaa cggggggcaa tgatac                    46


<210> SEQ ID NO 9
<211> LENGTH: 46
<212> TYPE: DNA
```

-continued

```
<213> ORGANISM: Artificial Sequence
<220> FEATURE:
<223> OTHER INFORMATION: Chemically Synthesized

<400> SEQUENCE: 9

gtatcattgc cccccgtttt acagtagaat agatcttcat tttcca                46
```